US010881659B2

(12) United States Patent
Chwalisz et al.

(10) Patent No.: US 10,881,659 B2
(45) Date of Patent: Jan. 5, 2021

(54) METHODS OF TREATING HEAVY MENSTRUAL BLEEDING

(71) Applicant: AbbVie Inc., North Chicago, IL (US)

(72) Inventors: Kristof Chwalisz, Mundelein, IL (US); Laura A. Williams, Gurnee, IL (US); Rita I. Jain, Evanston, IL (US); Janine D. North, Chicago, IL (US); Juki Wing-Keung Ng, Highland Park, IL (US)

(73) Assignee: ABBVIE INC., North Chicago, IL (US)

( * ) Notice: Subject to any disclaimer, the term of this patent is extended or adjusted under 35 U.S.C. 154(b) by 0 days.

(21) Appl. No.: 14/211,096

(22) Filed: Mar. 14, 2014

(65) Prior Publication Data

US 2014/0288031 A1 Sep. 25, 2014

Related U.S. Application Data

(60) Provisional application No. 61/788,821, filed on Mar. 15, 2013.

(51) Int. Cl.
| | |
|---|---|
| *A61K 31/513* | (2006.01) |
| *A61K 45/06* | (2006.01) |
| *A61K 31/565* | (2006.01) |
| *A61K 31/57* | (2006.01) |
| *A61P 15/00* | (2006.01) |

(52) U.S. Cl.
CPC .......... *A61K 31/513* (2013.01); *A61K 31/565* (2013.01); *A61K 31/57* (2013.01); *A61K 45/06* (2013.01); *A61P 15/00* (2018.01)

(58) Field of Classification Search
None
See application file for complete search history.

(56) References Cited

U.S. PATENT DOCUMENTS

| 6,225,298 B1 | 5/2001 | Spicer et al. |
| 7,700,559 B2 | 4/2010 | Millar et al. |
| 2016/0339037 A1 | 11/2016 | Trower |
| 2017/0056403 A1 | 3/2017 | Goss et al. |

FOREIGN PATENT DOCUMENTS

| WO | 0121194 A2 | 3/2001 |
| WO | 0121194 A3 | 3/2001 |
| WO | 2005007165 A1 | 1/2005 |
| WO | WO-2014143669 A1 | 9/2014 |
| WO | 2018060438 A1 | 4/2018 |
| WO | 2018224497 A1 | 12/2018 |

OTHER PUBLICATIONS

ASRM. Noncontraceptive Benefits of Birth Control Pills. 2011.*
ClinicalTrials.gov archive, Trial No. NCT01441635, 2011.*
Ehlers, K, Halvorson, L, Glob. libr. women's med., (ISSN: 1756-2228) 2013.*
Struthers RS, Nicholls AJ, Grundy J, et al. Suppression of Gonadotropins and Estradiol in Premenopausal Women by Oral Administration of the Nonpeptide Gonadotropin-Releasing Hormone Antagonist Elagolix. The Journal of Clinical Endocrinology and Metabolism. 2009;94(2):545-551.*
Adamson G.D., "Treatment of Uterine Fibroids: Current Findings With Gonadotropin-releasing Hormone Agonists.," American Journal of Obstetrics and Gynecology, 1992, vol. 166 (2), pp. 746-751.
Anonymous: "NCT01441635 on Sep. 27, 2011: Safety and Efficacy Pre-Menopausal Women With Heavy Uterine Bleeding and Uterine Fibroids", Clinicaltrials.gov Archive, [retrieved on Sep. 27, 2011]. Retrieved from the Internet: URL: http://clinicaltrials.gov/archive/NCT01441635/2011_09_27.
Anonymous: "NCT01817530 on Mar. 22, 2013: Safety and Efficacy in Premenopausal Women With Heavy Menstrual Bleeding (HMB) Associated With Uterine Fibroids (UF)", Clinicaltrials.gov Archive, [retrieved on Mar. 22, 2013]. Retrieved from the Internet: URL:http://clinicaltrials.gov/archive/NCTO 1817530/2013_03_22.
Baird D.D., et al., "High Cumulative Incidence of Uterine Leiomyoma in Black and White Women: Ultrasound Evidence.," American Journal of Obstetrics and Gynecology, 2003, vol. 188 (1), pp. 100-107.
Brown J.S., et al., "Hysterectomy and Urinary Incontinence: A Systematic Review.," Lancet, 2000, vol. 356 (9229), pp. 535-539.
Buttram V.C. Jr., et al., "Uterine Leiomyomata: Etiology, Symptomatology, and Management," Fertility and Sterility, 1981, vol. 36 (4), pp. 433-445.
Cardozo E.R., et al., "The Estimated Annual Cost of Uterine Leiomyomata in the United States.," American Journal of Obstetrics and Gynecology, 2012, vol. 206 (3), pp. e1-e9.
Carlson K.J., et al., "The Maine Women's Health Study: I. Outcomes of Hysterectomy.," Obstetrics and Gynecology, 1994, vol. 83 (4), pp. 556-565.
Carr B.R., et al., "An Evaluation of the Effect of Gonadotropin-releasing Hormone Analogs and Medroxyprogesterone Acetate on Uterine Leiomyomata Volume by Magnetic Resonance Imaging: A Prospective, Randomized, Double Blind, Placebo-controlled, Cross-over Trial.," The Journal of Clinical Endocrinology and Metabolism, 1993, vol. 76 (5), pp. 1217-1223.
Chwalisz K., et al., "Selective Progesterone Receptor Modulator Development and use in the Treatment of Leiomyomata and Endometriosis.," Endocrine Reviews, 2005, vol. 26 (3), pp. 423-438.

(Continued)

*Primary Examiner* — Craig D Ricci
(74) *Attorney, Agent, or Firm* — Neal, Gerber & Eisenberg LLP

(57) ABSTRACT

The present invention relates to the method of treating heavy menstrual bleeding in a subject with or without uterine fibroids and in need of treatment by administering an effective amount of 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethyl-amino)-butyric acid or a pharmaceutically acceptable salt thereof, in combination with estrogens and progestogens.

16 Claims, 5 Drawing Sheets

(56) References Cited

OTHER PUBLICATIONS

Daniels A., et al., "Treatment with the Gnrh Agonist (gnrha) Desorelin (d) and Low-dose Add-back Estradiol (e2) is Effective in Reducing Pain, Bleeding, and Uterine Volume (uv) while Maintaining Bmd in Women with Symptomatic Uterine Fibroids (uf).," Fertility and Sterility, 2002, vol. 78 (3 Suppl 1), pp. S65-S66.
FDA Approves Lysteda to Treat Heavy Menstrual Bleeding Silver Spring, MD; US Food and Drug Administration, Nov. 13, 2009. Reterived from http://www.fda.gov/NewsEvents/Newsroom/PressAnnouncements/ucm 190551.htm.
Friedman A.J., et al., "A Prospective, Randomized Trial of Gonadotropin-releasing Hormone Agonist Plus Estrogen-progestin or Progestin "add-back" Regimens for Women With Leiomyomata Uteri.," The Journal of Clinical Endocrinology and Metabolism, 1993, vol. 76 (6), pp. 1439-1445.
Hallberg L., et al., "Determination of Menstrual Blood Loss," Scandinavian Journal of Clinical and Laboratory Investigation, 1964, vol. 16, pp. 244-248.
Hendrix S.L., "Bilateral Oophorectomy and Premature Menopause.," The American Journal of Medicine, 2005, vol. 118 (Suppl 12B), pp. 131-135.
Hickey M., et al., "Superficial Endometrial Vascular Fragility in Norplant Users and in Women With Ovulatory Dysfunctional Uterine Bleeding.," Human Reproduction, 2000, vol. 15 (7), pp. 1509-1514.
International Search Report and Written Opinion for Application No. PCT/US2014/027673, dated May 27, 2014, 10 pages.
Lethaby A., et al., "Pre-operative Gnrh Analogue therapy Before Hysterectomy or Myomectomy for Uterine Fibroids.," The Cochrane Database of Systematic Reviews, 2009, vol. 1, pp. 1-97.
Maresh M.J., et al., "The Value National Hysterectomy Study: Description of the Patients and their Surgery.," BJOG , 2002, vol. 109 (3), pp. 302-312.
Maruo T., et al., "Effects of Progesterone on Uterine Leiomyoma Growth and Apoptosis.," Steroids, 2000, vol. 65 (10-11), pp. 585-592.
Myers E.R., et al., "Management of Uterine Leiomyomata: What Do We Really Know?," Obstetrics and Gynecology, 2002, vol. 100 (1), pp. 8-17.
North American Menopause Society, "Treatment of Menopause-associated Vasomotor Symptoms: Position Statement of the North American Menopause Society.," Menopause, 2004, vol. 11 (1), pp. 11-33.
Sabry M., et al., "Innovative Oral Treatments of Uterine Leiomyoma," Obstetrics and Gynecology International, 2012, vol. 30 (1), pp. 1-10.
Sabry M., et al., "Medical Treatment of Uterine Leiomyoma," Reproductive Sciences, 2012, vol. 19 (4), pp. 339-353.
Simbar M., et al., "A Three-dimensional Study of Endometrial Microvessels in Women Using the Contraceptive Subdermal Levonorgestrel Implant System, Norplant.," Micron, 2004, vol. 35 (7), pp. 589-595.
Stewart A., et al., "The Effectiveness of the Levonorgestrel-releasing Intrauterine System in Menorrhagia: A Systematic Review.," BJOG , 2001, vol. 108 (1), pp. 74-86.
Stewart E.A., "Uterine Fibroids.," Lancet, 2001, vol. 357 (9252), pp. 293-298.
Stovall T.G., "Gonadotropin-releasing Hormone Agonists: Utilization Before Hysterectomy.," Clinical Obstetrics and Gynecology, 1993, vol. 36 (3), pp. 642-649.
The Menorrhagia Research Group, "Quantification of Menstrual Blood Loss.," The Obstetrician & Gynaecologist., 2004, vol. 6, pp. 88-92.
Tiltman A.J., "The Effect of Progestins on the Mitotic Activity of Uterine Fibromyomas.," International Journal of Gynecological Pathology, 1985, vol. 4 (2), pp. 89-96.
Welsh A, Heavy Menstrual Bleeding, ed. London: RCOG Press at Royal College of Obstetricians and Gynaecologists; 2007.
Bhatia K., et al., "A Randomised Controlled Trial Comparing GnRH Antagonist Cetrorelix with GnRH agonist Leuprorelin for Endometrial Thinning Prior to Transcervical Resection of Endometrium," BJOG: An International Journal of Obstetrics & Gynaecology, 2008, vol. 115 (10), pp. 1214-1224.
Supplementary International Search Report for Application No. PCT/US2014/027673, dated Dec. 19, 2014, 5 pages.
Surrey E.S., "Steroidal and Nonsteroidal "Add-back" Therapy: Extending Safety and Efficacy of Gonadotropin-Releasing Hormone Agonists in the Gynecologic Patient," Fertility and Sterility, 1995, vol. 64 (4), pp. 673-685.
International Search Report and Written Opinion for Application No. PCT/US2018/28390, dated Aug. 8, 2018, 17 pages.
Felberbaum, R.E., et al., "Will GnRH antagonists assist in the treatment of benign gynaecological diseases?" Reproductive BioMedicine Online, 2002, vol. 5 Suppl. 1, pp. 68-72.
Felberbaum, R.E., et al., "Treatment of uterine fibroids with a slow-release formulation of the gonadotrophin releasing hormone antagonist Cetrorelix," Human Reproduction, 1998, vol. 13(6), pp. 1660-1668.
Kuper, W., et al., "Use of GnRH antagonists in the treatments of endometriosis," Reproductive BioMedicine Online, 2002, vol. 5(1), pp. 12-16.
Taylor H.S., et al., "Treatment of Endometriosis-Associated Pain with Elagolix, an Oral GnRH Antagonist," The New England Journal of Medicine, 2017, vol. 377, pp. 28-40.
Carr B., et al., "Elagolix, an Oral GnRH Antagonist, Versus Subcutaneous Depot Medroxyprogesterone Acetate for the Treatment of Endometriosis: Effects on Bone Mineral Density," Reproductive sciences, 2014, vol. 21 (11), pp. 1341-1351.
Extended European Search Report for Application No. EP18171240, dated Sep. 6, 2018, 5 pages.
International Search Report and Written Opinion for Application No. PCT/US2018/043321, dated Oct. 30, 2018, 9 pages.
NCT00797225 (published Feb. 6, 2012) (Year: 2012), 6 pages.
Supplementary European Search Report for Application No. EP14717031, dated Sep. 23, 2015, 4 pages.
Denny E., et al., "Endometriosis-associated dyspareunia: the impact on women's lives," Journal of Family Planning and Reproductive Health Care, 2007, vol. 33 (3), pp. 189-193.
International Search Report and Written Opinion for Application No. PCT/US2019/044613, dated Oct. 25, 2019, 14 pages.

* cited by examiner

METHODS OF TREATING HEAVY MENSTRUAL BLEEDING

CROSS REFERENCE TO RELATED APPLICATIONS

This claims priority to U.S. Patent Application No. 61/788,821, filed on Mar. 15, 2013, the entire contents of which are fully incorporated herein by reference.

FIELD OF THE INVENTION

This invention pertains to the use of GnRH receptor antagonists for the treatment of heavy menstrual bleeding in a subject with or without uterine fibroids.

BACKGROUND OF THE INVENTION

Uterine fibroids (leiomyomata) are the most common benign tumors in women. Uterine fibroids are highly prevalent in women of reproductive age and are identified in more than 50% of women between 35 and 50 years of age. The incidence increases with age and is the most common reason for hysterectomy (Buttram V C Jr, Reiter R C. Uterine leiomyomata: etiology, symptomatology, and management. *Fertil Steril.* 1981; 36(4):433-45; Day Baird D, Dunson D B, Hill M C, et al. High cumulative incidence of uterine leiomyoma in black and white women: ultrasound evidence. *Am J Obstet Gynecol.* 2003; 188(1):100-7).

The estimated annual direct costs of symptomatic uterine fibroids (surgery, hospital admissions, outpatient visits, and medications) are $4.1 to 9.4 billion. Estimated lost work-hour costs range from $1.55-17.2 billion annually. Obstetric outcomes attributed to fibroid tumors result in a cost of $238 million to $7.76 billion annually. Overall, uterine fibroid tumors were estimated to cost the United States $5.9-34.4 billion annually (Cardozo E R, Clark A D, Banks N K, et al. The estimated annual cost of uterine leiomyomata in the United States. *Am J Obstet Gynecol* 2012; 206:211.e1-9).

Although often asymptomatic, fibroids may cause symptoms severe enough to warrant therapy in 20% to 50% of women. Symptoms associated with fibroids most commonly include heavy or prolonged menstrual bleeding, pelvic pressure and pelvic organ compression, back pain, and adverse reproductive outcomes. Heavy menstrual bleeding (HMB; menorrhagia, defined as greater than 80 mL per menstrual cycle) (The Menorrhagia Research Group. Quantification of menstrual blood loss. *The Obstetrician & Gynaecologist.* 2004; 6:88-92) is inconvenient and may lead to iron-deficiency anemia, a key symptom of uterine fibroids and the leading cause of surgical interventions that may include hysterectomy. Other symptoms, in particular pressure symptoms, are largely dependent on the size, number, and location of the tumors.

Uterine fibroids are highly heterogeneous tumors with variable growth rates and symptomatology. Therefore, the choice of treatment is based on individual symptoms, patient preference, and the desire to preserve either fertility or the uterus, or both. Historically, hysterectomy or myomectomy were preferred treatment options for women with symptomatic uterine fibroids (Stewart E A. Uterine fibroids. *Lancet,* 2001; 357:293-8; Myers E R, Barber M D, Gustilo-Ashby T, et al. Management of uterine leiomyomata: what do we really know? *Obstet Gynecol.* 2002;100(1):8-17). However, surgery is also associated with risks such as infections, bleeding complications, thromboembolic effects, scarring/adhesions, and even increased mortality (Maresh M J A, Metcalfe M A, McPherson K, et al. The VALUE national hysterectomy study: description of the patients and their surgery. *Br J Obstet Gynaecol.* 2002; 109(3):302-12). The mortality rate for hysterectomy for benign indications is approximately 0.38 per 1,000 cases (Maresh M J A, Metcalfe M A, McPherson K, et al. The VALUE national hysterectomy study: description of the patients and their surgery. *Br J Obstet Gynaecol.* 2002; 109(3):302-12). Furthermore, many women opt not to have a hysterectomy for cultural or reproductive reasons. The long-term side effects of hysterectomy may include higher rates of depression in younger women and incontinence in women at least 60 years old (Brown J S, Sawaya G, Thom D H, et al. Hysterectomy and urinary incontinence: a systematic review. Lancet, 2000; 356:535-39; Carlson K J, Miller B A, Fowler F J Jr. The Maine Women's Health Study: I. Outcomes of hysterectomy. *Obstet Gynecol.* 1994; 83(4):556-65). As more women delay maternity into their 30s and 40s, there is a growing need for alternatives to surgical treatments, especially hysterectomy. To meet this demand, during the past two decades, many new uterus-sparing therapies have been proposed and studied including semi-invasive procedures, such as uterine artery embolization and magnetic resonance imaging (MRI)-guided high-intensity focused ultrasound ablation therapy as well as nonsurgical, medical treatments. Of note, none of these uterus-sparing methods provide definitive cure, as fibroids often recur following treatment.

Although the pathogenesis has yet to be fully elucidated, the growth of uterine fibroids is known to be highly dependent on both estrogen and progestogen. This dependence on ovarian hormones is evidenced by the spontaneous reduction in fibroid size commonly observed after menopause, a natural anovulatory and hypoestrogenic state. On this basis, most medical treatments for women with symptomatic uterine fibroids are aimed at either hormone-blocking or hormone-modulating strategies.

The ideal medical treatment for symptomatic uterine fibroids, as an alternative to surgical interventions, should provide control of heavy menstrual bleeding, reduce fibroid and uterine volume, improve quality of life, and prove safe and tolerable as a chronic therapy. Unfortunately, currently available medical options provide only short-term improvement of symptoms, and as such, are only indicated prior to surgery or their side-effects limit their long-term use. A safe and effective chronic medical therapy for symptomatic uterine fibroids, as an alternative to hysterectomy or other surgical intervention, has not yet been approved.

Currently there are no chronic treatments approved for the long term management of heavy menstrual blood loss associated with symptomatic uterine fibroids. However, in the United States, leuprolide acetate (Lupron®) in combination with iron is approved for the preoperative short-term treatment of women with uterine fibroids to improve hematological parameters (Stovall T G. Gonadotropin-releasing hormone agonists: utilization before hysterectomy. *Clin Obstet Gynecol.* 1993; 36(3):642-9; Lupron Depot (leuprolide acetate for depot suspension) injection, powder, lyophilized, for suspension [package insert]. North Chicago, Ill.; Abbott, January 2011; Lethaby A, Vollenhoven B, Sowter M C. Pre-operative GnRH analogue therapy before hysterectomy or myomectomy for uterine fibroids. *Cochrane Database of Syst Rev.* 2009; 1:1-97). Beside the preoperative treatment, different medical treatments have been used for the management of heavy menstrual bleeding associated with uterine fibroids that include tranexamic acid, combined oral contraceptives, levonorgestrel intrauterine system (LNG-IUS), high-dose progestins, androgens (danazol), progestogen receptor modulators, GnRH agonists, and GnRH antagonists (*Heavy Menstrual Bleeding*. Welsh A, ed. London: RCOG Press at Royal College of Obstetricians and Gynaecologists; 2007; Stewart A, Cummins C, Gold L, et al. The effectiveness of levonorgestrel-releasing intrauterine system in menorrhagia: a systematic review. BJOG. 2001; 108(1):74-86; Lethaby A, Vollenhoven B, Sowter M C. Pre-operative GnRH analogue therapy before hysterectomy or myomectomy for uterine fibroids. *Cochrane Database of Syst Rev.* 2009; 1:1-97; Carr B R, Marshburn P B, Weatherall P T, et al. An evaluation of the effect of gonadotropin releasing hormone analogs and medroxyprogesterone acetate on uterine leiomyomata volume by magnetic resonance imaging: a prospective, randomized, double-blind, placebo-controlled, crossover trial. *J Clin Endocrinol Metab.* 1993; 76(5):1217-23; Friedman A M, Daly M, Juneau-Norcross M, et al. A prospective, randomized trial of gonadotropin-releasing hormone agonist plus estrogen progestin or progestin add-back regimens for women with leiomyomata uteri. *J Clin Endocrinol Metab.* 1993; 76(6): 1439-45; Adamson G D. Treatment of uterine fibroids: current findings with gonadotropin-releasing hormone agonists. *Am J Obstet Gynecol.* 1992; 166:746-51; Stovall T G. Gonadotropin-releasing hormone agonists: utilization before hysterectomy. *Clin Obstet Gynecol.* 1993; 36(3):642-9). All these treatments are variously effective in reducing heavy menstrual bleeding, but only a few (namely, GnRH agonists, androgens, aromatase inhibitors) also reduce fibroid and uterine volume.

The antifibrinolytic drug, tranexamic acid has been widely used for more than 2 decades outside the United States for the management of heavy menstrual bleeding and was approved in 2009 in the United States for the management of heavy menstrual bleeding in women with or without uterine fibroids (FDA approves Lysteda to treat heavy menstrual bleeding [press release]. Silver Spring, Md.; US Food and Drug Administration, 13 Nov. 2009. Available from http://www.fda.gov/NewsEvents/Newsroom/PressAnnouncements/ucm190551.htm. Accessed on: 19 Jun. 2012).

Although combined oral contraceptives (OCs) are widely used for the treatment of women complaining of anovulatory bleeding, to date, there are no high-quality comparative studies supporting their use in heavy menstrual bleeding associated with uterine fibroids. Nevertheless, combined OCs are frequently used for the temporary management of heavy menstrual bleeding. Epidemiological studies indicate that combined OCs are neutral in terms of their effects on fibroid growth or prevalence.

The levonorgestrel intrauterine system ("LNG-IUS") has been approved for the management of heavy menstrual bleeding in women who use intrauterine contraception as their method of pregnancy prevention. However, LNG-IUS may only be used in women who have no distortion of the uterine cavity. Additionally, oral high-dose progestins are the most commonly prescribed therapy for short-term management of heavy menstrual bleeding not associated with uterine fibroids. However, little evidence supports the use of progestins in the presence of uterine fibroids and high-dose progestin may stimulate fibroid growth when used continuously as a monotherapy, or in conjunction with a GnRH agonist as add-back therapy (Carr B R, Marshburn P B, Weatherall P T, et al. An evaluation of the effect of gonadotropin releasing hormone analogs and medroxyprogesterone acetate on uterine leiomyomata volume by magnetic resonance imaging: a prospective, randomized, double-blind, placebo-controlled, crossover trial. *J Clin Endocrinol Metab.* 1993; 76(5):1217-23; Friedman A M, Daly M, Juneau-Norcross M, et al. A prospective, randomized trial of gonadotropin-releasing hormone agonist plus estrogen progestin or progestin add-back regimens for women with leiomyomata uteri. *J Clin Endocrinol Metab.* 1993; 76(6): 1439-45). In addition, continuous use of progestins may actually induce breakthrough bleeding and spotting via negative effects on normal endometrial angiogenesis (Hickey M, Dwarte D, Fraser I S. Superficial endometrial vascular fragility in Norplant users and in women with ovulatory dysfunctional uterine bleeding. Hum Reprod 2000; 15:1509-14) and may increase endometrial vascular fragility (38 Simbar et al., 2004).

Clinical data from registration studies with leuprolide acetate (Lupron Depot®) (Lupron Depot® (leuprolide acetate for depot suspension) injection, powder, lyophilized, for suspension [package insert]. and a review of the literature, indicate that GnRH agonists are effective at inducing amenorrhea, improving anemia in women with symptomatic uterine fibroids, and substantially reducing uterine and fibroid volumes. GnRH agonists provide a 30% to 50% reduction in fibroid volume within 3 months of treatment (Carr B R, Marshburn P B, Weatherall P T, et al. An evaluation of the effect of gonadotropin releasing hormone analogs and medroxyprogesterone acetate on uterine leiomyomata volume by magnetic resonance imaging: a prospective, randomized, double-blind, placebo-controlled, crossover trial. *J Clin Endocrinol Metab.* 1993; 76(5):1217-23; Friedman A M, Daly M, Juneau-Norcross M, et al. A prospective, randomized trial of gonadotropin-releasing hormone agonist plus estrogen progestin or progestin add-back regimens for women with leiomyomata uteri. *J Clin Endocrinol Metab.* 1993; 76(6):1439-45). In addition, the side effects of estrogen deprivation, primarily bone mineral density (BMD) loss and severe hot flushes, limit the use of GnRH agonists. In fact, menopausal symptoms in women with surgically-induced menopause (which is similar to GnRH agonist-induced menopause) are more severe than symptoms in women who undergo menopause naturally (Treatment of menopause-associated vasomotor symptoms: position statement of The North American Menopause Society. *Menopause,* 2004:11(1):11-33; Hendrix S. Bilateral oophorectomy and premature menopause. *Am J Med.* 2005; 118 (12 Suppl 2):131-5). Furthermore, the effects on the uterus are reversible, gradual regrowth of fibroids occurs within months of treatment cessation.

Concerns about bone loss and poor tolerability of GnRH agonist monotherapy led to a number of studies whereby various potential add-back therapies were added to these GnRH-agonist regimens. In contrast to the management of endometriosis, there are no FDA-approved add-back therapies for use with GnRH agonists for women with uterine fibroids. Early trials focused on progestin-only add-back therapies, including medroxyprogesterone acetate (15-20 mg/day orally) or norethindrone (10 mg/day orally), and there was a reduction of hot flashes but the reduction in uterine or uterine fibroid volume was significantly limited (Carr B R, Marshburn P B, Weatherall P T, et al. An evaluation of the effect of gonadotropin releasing hormone analogs and medroxyprogesterone acetate on uterine leiomyomata volume by magnetic resonance imaging: a prospective, randomized, double-blind, placebo-controlled, crossover trial. *J Clin Endocrinol Metab.* 1993; 76(5):1217-23). The effect of progestin-only add-back therapy on uterine bleeding was not reported in these studies, although treatment with high-dose progestins is known to be associated with breakthrough bleeding and spotting.

Studies with progestogen receptor modulators (mifepristone, asoprisnil, ulipristal acetate) in this population (Chwalisz K, Perez M C, DeManno D, et al. Selective progestogen receptor modulator development and use in the treatment of leiomyomata and endometriosis. Endoc Rev 2005; 26(3): 423-38), as well as previous experience with high-dose progestins (Carr B R, Marshburn P B, Weatherall P T, et al. An evaluation of the effect of gonadotropin releasing hormone analogs and medroxyprogesterone acetate on uterine leiomyomata volume by magnetic resonance imaging: a prospective, randomized, double-blind, placebo-controlled, crossover trial. *J Clin Endocrinol Metab.* 1993; 76(5):1217-23; Friedman A M, Daly M, Juneau-Norcross M, et al. A prospective, randomized trial of gonadotropin-releasing hormone agonist plus estrogen progestin or progestin add-back regimens for women with leiomyomata uteri. *J Clin Endocrinol Metab.* 1993; 76(6):1439-45) indicate that uterine fibroids are highly progestogen-dependent. In contrast to other uterine tissues, high doses of progestins were shown to exert proliferative effects on uterine fibroids and these data explain the failure of progestin-based add-back therapy in women with uterine fibroids (Tiltman A. The effects of progestins on the mitotic activity of uterine fibromyomas. Int J Gynecol Pathol. 1985; 4:89-96; Maruo T, Matsuo H, Samoto T. et al. Effects of progestogen on uterine leiomyoma growth and apoptosis. Steroids. 2000; 65:585-92). High-dose progestin treatment is also associated with uterine bleeding abnormalities such as breakthrough bleeding and spotting, and systemic side effects, including weight gain and metabolic effects (Hickey M, Dwarte D, Fraser I S. Superficial endometrial vascular fragility in Norplant users and in women with ovulatory dysfunctional uterine bleeding. *Hum Reprod* 2000; 15:1509-14; Simbar M, Manconi F, Markham, R, et al. A three-dimensional study of endometrial microvessels in women using the contraceptive subdermal levonorgestrel implant system, norplant. *Micron.* 2004; 35:589-95).

More recently, the effectiveness of low-dose E2 as add-back therapy when used in combination with GnRH agonists was demonstrated in 185 women with heavy menstrual bleeding associated with uterine fibroids (Daniels A, Pike M C, et al; Balance Pharmaceuticals Uterine Fibroids Study Group. Treatment with the GnRH agonist (GnRHa) desorelin (D) and low-dose add-back estradiol (E2) is effective in reducing pain, bleeding, and uterine volume (UV) while maintaining BMD in women with symptomatic uterine fibroids (UF). *Fertil Steril.* 2002; 78(3, Suppl 1):O-170). These findings showed that the efficacy (reduction in uterine bleeding and volume) of deslorelin, a GnRH agonist, was maintained when dosed with low-dose transdermal E2, while mitigating significant BMD loss through 6 months of treatment. However, the chronic use of estrogen alone (without a progestin) as add-back therapy is not feasible because of the risk of unopposed estrogen effect on the endometrium that may lead to endometrial hyperplasia.

Therefore, there is a need in the art for new treatment methods for reducing or managing heavy menstrual blood loss and other symptoms associated with symptomatic uterine fibroids.

BRIEF SUMMARY OF THE INVENTION

The present invention relates to methods for reducing the volume of menstrual blood loss in a subject with or without uterine fibroids. The present invention also relates to a method for reducing the fibroid and uterine volume and treatment for non-bleeding-related symptoms of uterine fibroids. The methods comprise administering to a subject 300 to 600 mg per day of 4-((R)-2-[5-(2-fluoro-3-methoxy-phenyl)-3-(2-fluoro-6-trifluoromethyl-benzyl)-4-methyl-2, 6-dioxo-3,6-dihydro-2H-pyrimidin-1-yl]-1-phenyl-ethyl-amino)-butyric acid or a pharmaceutically acceptable salt thereof, in combination with estrogens and progestogens. In the above methods, the estrogen is selected from the group consisting of estradiol, ethinyl estradiol, and conjugated estrogens, and the progestogen is selected from the group consisting of progesterone, norethindrone acetate, norgestimate, drospirenone, and medroxyprogesterone. For example, in the above methods, the estrogen is estradiol and the progestogens are norethindrone acetate and progesterone.

Subjects in need of treatment thereof have a volume of menstrual blood greater than 80 mL per menstrual cycle. Once said subjects are treated according to the above methods, these subjects have a volume of menstrual blood loss that is less than 80 mL per menstrual cycle.

Subjects treated according to the above methods can have uterine fibroids or do not have uterine fibroids.

Subjects treated according to the above methods can have non-bleeding symptoms related to uterine fibroids ("bulk symptoms") such as pelvic pressure, bloating, pelvic pain, urinary problems, etc.

In the above methods, the estradiol and norethindrone acetate (which is a progestogen) are administered orally once per day. For example, in one aspect, the estradiol is administered in an amount of about 0.5 mg and the norethindrone acetate is administered in an amount of about 0.1 mg per day. In another aspect, the estradiol is administered in an amount of about 1.0 mg and the norethindrone acetate is administered in an amount of about 0.5 mg per day. Alternatively, the estradiol is administered continuously and the norethindrone acetate is administered once per day during the last 12-14 days of a menstrual cycle.

In the above methods, the 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid or a pharmaceutically acceptable salt thereof is administered in an amount of about 300 mg per day. Specifically, the 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid or a pharmaceutically acceptable salt thereof is administered twice per day.

In the above methods, the 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid or a pharmaceutically acceptable salt thereof is administered in an amount of about 400 mg per day. Specifically, the 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid or a pharmaceutically acceptable salt thereof is administered twice per day.

In the above methods, the 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid or a pharmaceutically acceptable salt thereof is administered in an amount of about 600 mg per day. Specifically, the 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid or a pharmaceutically acceptable salt thereof is administered twice per day.

In the above methods, the 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid, estrogens, and progestogens are administered daily for at least 28 days. In another aspect, the 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid, estrogens, and progestogens are administered daily for at least 56 days. In yet still another aspect, the 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid, estrogens, and progestogens are administered daily for at least 84 days. In still yet another aspect, the 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid, estrogens, and progestogens are administered daily for at least 168 days. In still yet another aspect, the 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid, estrogens, and progestogens are administered daily for about 168 days to about 1 year.

The present invention also relates to a method for treating uterine fibroids in a subject in need of treatment. The method comprises administering to the subject 300 to 600 mg per day of 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid or a pharmaceutically acceptable salt thereof, in combination with estrogens and progestogens. For example, in the above method, the estrogen is estradiol and the progestogens are norethindrone acetate and progesterone.

In the above method, the estradiol and norethindrone acetate are administered once per day. For example, in one aspect, the estradiol is administered in an amount of about 0.5 mg and the norethindrone acetate is administered in an amount of about 0.1 mg per day. In another aspect, the estradiol is administered in an amount of about 1.0 mg and the norethindrone acetate is administered in an amount of about 0.5 mg per day.

In the above method, the 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid or a pharmaceutically acceptable salt thereof is administered in an amount of about 300 mg per day. Specifically, the 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid or a pharmaceutically acceptable salt thereof is administered twice per day.

In the above method, the 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid or a pharmaceutically acceptable salt thereof is administered in an amount of about 400 mg per day. Specifically, the 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid or a pharmaceutically acceptable salt thereof is administered twice per day.

In the above method, the 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid or a pharmaceutically acceptable salt thereof is administered in an amount of about 600 mg per day. Specifically, the 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid or a pharmaceutically acceptable salt thereof is administered twice per day.

In the above method, the 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid, estrogens, and progestogens are administered daily for at least 28 days. In another aspect, the 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid, estrogens, and progestogens are administered daily for at least 56 days. In yet still another aspect, the 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid, estrogens, and progestogens are administered daily for at least 84 days. In still yet another aspect, the 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid, estrogens, and progestogens are administered daily for at least 168 days. In still yet another aspect, the 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid, estrogens, and progestogens are administered daily for about 168 days to about 1 year.

BRIEF DESCRIPTION OF THE FIGURES

FIG. 1 shows the last observation carried forward (LOCF) for the last 28 days of treatment in all subjects. The composite bleeding endpoint shown on the left was calculated using alkaline hematin data. Amenorrhea was calculated using both alkaline hematin data and a daily bleeding diary data. For each of the Composite Bleeding Endpoint and Amenorrhea bar graphs shown in FIG. 1, patients were treated with Elagolix 300 BID (N=30) (first bar on the far left), E600 QD (N=28) (second bar from the left), E300+estrogen (1.0 mg of estradiol (Estrace®)) and 200 mg progesterone (cyclical Prometrium®) (collectively referred to as "EP") (N=26) (third bar from the left), E200 BID (N=33) (fourth bar from the left), E400 QD (N=31) (fifth bar from the left), E200 BID+a low dose Activella® (a combination of 0.5 mg estradiol and 0.1 mg northindrone acetate) (referred to as "A") (N=34) (sixth bar from the left), E100 BID (seventh bar from the left) (N=31) and placebo (PBO) (N=49) (eighth bar from the left (or first on the right)). P values are defined as: *p<0.001 for Elagolix vs. pooled placebo (PBO; PBO from cohorts 1, 2 & 4). p<0.01 for Elagolix vs. pooled PBO (PBO from cohorts 1, 2 & 4).

DETAILED DESCRIPTION OF THE INVENTION

Definitions

Figure 1:
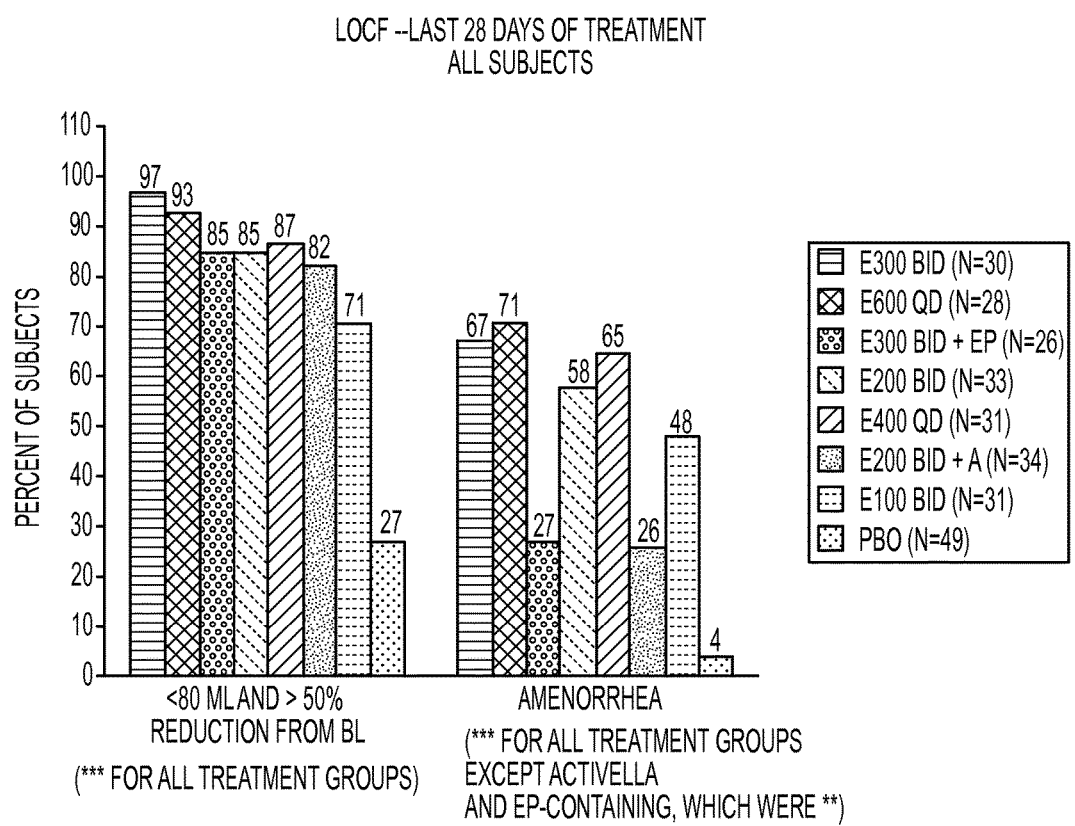
FIG. 1 shows the composite bleeding endpoint (percentage of subjects with blood loss reduction<80 ml/cycle and ≥50% reduction in blood loss compared to baseline) and amenorrhea (no bleeding or spotting) for the study described in Example 1.

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. In this application, the use of "or" means "and/or" unless stated otherwise. Furthermore, the use of the term "including", as well as other forms, such as "includes" and "included", is not limiting. With reference to the use of the words "comprise" or "comprises" or "comprising" in this patent application (including the claims), Applicants note that unless the context requires otherwise, those words are used on the basis and clear understanding that they are to be interpreted inclusively, rather than exclusively, and that Applicants intend each of those words to be so interpreted in construing this patent application, including the claims below. For a variable that occurs more than one time in any substituent or in the compound of the invention or any other formulae herein, its definition on each occurrence is independent of its definition at every other occurrence.

The term "Elagolix" refers to 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid or a pharmaceutically acceptable salt thereof. Elagolix is an orally active, non-peptide GnRH antagonist and is unlike other GnRH agonists and injectable (peptide) GnRH antagonists. Elagolix produces a dose dependent suppression of pituitary and ovarian hormones in women. Methods of making Elagolix and a pharmaceutically acceptable salt thereof are described in WO 2005/007165, the contents of which are herein incorporated by reference.

Elagolix or 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid may generally be utilized as the free acid or free base. Alternatively, Elagolix or 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid may be used in the form of acid or base addition salts. Acid addition salts of the free amino compounds of the present invention may be prepared by methods well known in the art, and may be formed from organic and inorganic acids. Suitable organic acids include maleic, fumaric, benzoic, ascorbic, succinic, methanesulfonic, acetic, trifluoroacetic, oxalic, propionic, tartaric, salicylic, citric, gluconic, lactic, mandelic, cinnamic, aspartic, stearic, palmitic, glycolic, glutamic, and benzenesulfonic acids. Suitable inorganic acids include hydrochloric, hydrobromic, sulfuric, phosphoric, and nitric acids. Base addition salts included those salts that form with the carboxylate anion and include salts formed with organic and inorganic cations such as those chosen from the alkali and alkaline earth metals (for example, lithium, sodium, potassium, magnesium, barium and calcium), as well as the ammonium ion and substituted derivatives thereof (for example, dibenzylammonium, benzylammonium, 2-hydroxyethylammonium, and the like). Thus, the term "pharmaceutically acceptable salt" of Elagolix or 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid is intended to encompass any and all acceptable salt forms.

In addition, Elagolix or 4-((R)-2-[5-(2-fluoro-3-methoxyphenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid or salts thereof may also form solvates with water or other organic solvents. Such solvates are similarly included within the scope of this invention.

The terms "treat", "treating" and "treatment" refer to a method of alleviating or abrogating a disease and/or its attendant symptoms.

By "pharmaceutically acceptable" it is meant the carrier, diluent or excipient must be compatible with the other ingredients of the formulation and not deleterious to the recipient thereof.

"Solvate" of a compound refers to a molecular complex of the solute (the compound) and the solvent.

The "subject" is defined herein to include animals such as mammals, including, but not limited to, primates (e.g., humans) and the like. In preferred embodiments and aspects, the subject is a human female. In yet another embodiment or aspect, the subject is a premenopausal human female.

"Effective amount" or a "pharmaceutically-effective amount" in reference to Elagolix or 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid, or salts thereof, or estrogens or progestogens refers to the amount sufficient to induce a desired biological, pharmacological, or therapeutic outcome in a subject.

Methods of Reducing or Managing Heavy Menstrual Bleeding Associated with Uterine Fibroids In one embodiment, the present invention relates to methods for reducing or managing heavy menstrual bleeding (HMB) associated with uterine fibroids in subjects in need of treatment thereof. Heavy menstrual bleeding refers to a subject experiencing greater than 80 mL of blood loss per menstrual cycle (a menstrual cycle is typically 28 days). In contrast, women who do not suffer from heavy menstrual bleeding experience about 30-40 mL of blood loss per menstrual cycle. In one aspect, the methods of the present invention can be used to reduce or manage heavy menstrual bleeding in a subject with uterine fibroids to an amount less than 80 mL of blood loss per cycle. In another aspect, the methods of the present invention can be used to reduce the volume of heavy menstrual bleeding in the subject with uterine fibroids by at least 50% from baseline.

Methods for analyzing menstrual blood loss are known in the art and include, for example, the alkaline hematin method. The alkaline hematin method is based on the quantitation of menstrual blood collected on sanitary products (Hallberg L., Nilsoon L., Determination of Menstrual Blood Loss. *Scand. J. Clin. Lab. Invest.*, 1964; 16:244-248). The method uses a strong alkaline solution to chemically convert the heme from bloodstained sanitary products to alkaline hematin, which is measured colorimetrically. When compared to a subject's serum hemoglobin (Hgb), the volume of blood loss in the menstrual products can be determined.

a. Use of Elagolix or a Pharmaceutically Acceptable Salt Thereof

In one aspect, the methods of the present invention involve reducing or managing heavy menstrual bleeding associated with uterine fibroids in a subject in need of treatment thereof. The methods involve administering to a subject suffering from heavy menstrual bleeding associated with uterine fibroids an effective amount of Elagolix or a pharmaceutically acceptable salt thereof. The effective amount or dose of Elagolix or a pharmaceutically acceptable salt thereof that can be administered to a subject is in the range of 300 to 600 mg. In a further aspect of the invention, the effective amount or dose of Elagolix or a pharmaceutically acceptable salt or solvate thereof is about 300 mg, 400 mg, or 600 mg per day. In still yet another aspect of the invention, the effective amount or dose of Elagolix or a pharmaceutically acceptable salt or solvate thereof is about 300 mg per day. In still yet another aspect of the invention, the effective amount or dose of Elagolix or a pharmaceutically acceptable salt or solvate thereof is about 400 mg per day. In still yet another aspect of the invention, the effective amount or dose of Elagolix or a pharmaceutically acceptable salt or solvate thereof is about 600 mg per day. The dose can be administered once a day or twice a day.

b. Use of Elagolix or a Pharmaceutically Acceptable Salt Thereof in Combination with Hormone Replacement Therapy In another aspect, the methods of the present invention involve reducing or managing heavy menstrual bleeding associated with uterine fibroids in a subject in need of treatment thereof. The methods involve administering to a subject suffering from heavy menstrual bleeding associated with uterine fibroids an effective amount of Elagolix or a pharmaceutically acceptable salt thereof in combination with one or more estrogens and progestogens. The administration of a combination of estrogen and progestogens to subjects is often referred to as "hormone replacement therapy" or "add-back therapy". The "hormone replacement therapy" or "add-back therapy" is used to prevent hypoestrogenic symptoms such as bone mineral density loss and vasomotor symptoms. Specifically, it was found that when subjects were treated with an effective amount of Elagolix or a pharmaceutically acceptable salt thereof in combination with the estrogens and progestogens, substantially lower number of subjects reported hot flashes (which are a vasomotor symptom of estrogen deprivation) compared to those treated with Elagolix alone.

The effective amount or dose of Elagolix or a pharmaceutically acceptable salt thereof that can be administered to a subject is in the range of 300 to 600 mg per day. In a further aspect of the invention, the effective amount or dose of Elagolix or a pharmaceutically acceptable salt or solvate thereof is about 300 mg, 400 mg, or 600 mg per day. In still yet another aspect of the invention, the effective amount or dose of Elagolix or a pharmaceutically acceptable salt or solvate thereof is about 300 mg per day. In still yet another aspect of the invention, the effective amount or dose of Elagolix or a pharmaceutically acceptable salt or solvate thereof is about 400 mg per day. In still yet another aspect of the invention, the effective amount or dose of Elagolix or a pharmaceutically acceptable salt or solvate thereof is about 600 mg per day. The effective amount or dose can be administered once a day or twice a day. The estrogen and/or progestogens can be administered orally, transdermally or intravaginally.

Suitable estrogens that can be used include, for example, estradiol, ethinyl estradiol, and conjugated estrogens.

Suitable progestogens that can be used include, for example, progesterone, norethindrone, norethindrone acetate, norgestimate, drospirenone, and medroxyprogestogen.

Combined oral formulations, used continuously, containing estrogens and progestogens for hormone replacement therapy are known in the art and can also be used in the invention. Suitable formulations include, for example, Activella®, Angeliq®, FemHRT®, Jenteli™, Mimvey™, Prefest™, Premphase®, and Prempro®.

In one aspect of the invention, the estrogen is estradiol. In another aspect, the dose of estradiol is 0.5 mg. In another embodiment, the dose of estradiol is 1.0 mg. In yet another embodiment, the estradiol is administered once a day.

In another aspect of the invention, the estrogen is ethinyl estradiol. In another embodiment, the dose of ethinyl estradiol is 2.5 mcg. In yet another embodiment, the dose of estradiol is 5.0 mcg. In still yet another aspect, the ethinyl estradiol is administered once a day.

In still yet another aspect of the invention, the estrogen is conjugated estrogens. In another embodiment, the dose of conjugated estrogens is 0.3 mg. In still yet another embodiment, the dose of conjugated estrogens is 0.45 mg or 0.625 mg. In still yet another embodiment, the conjugated estrogens is administered once a day.

In still yet another aspect of the invention, the progestogen is oral progesterone, which is used cyclically (for the last 12 days of the 28-30 day cycle). In another embodiment, the dose of progesterone is 100 or 200 mg.

In still yet another aspect of the invention, the progestogen is norethindrone or norethindrone acetate. In another aspect, the dose of norethindrone or norethindrone acetate is 0.1 mg. In another aspect, the dose of norethindrone or norethindrone acetate is 0.5 mg. In another embodiment, the dose of norethindrone or norethindrone acetate is 1.0 mg. In yet another aspect, the norethindrone or norethindrone acetate is administered once a day.

In still yet another aspect of the invention, the progestogen is norgestimate. In another aspect, the dose of norgestimate is 0.09 mg. In still yet another aspect, the norgestimate is administered once a day.

In still yet another aspect of the invention, the progestogen is medroxyprogesterone. In still yet another aspect of the invention, the dose of medroxyprogesterone is 1.5 mg. In another aspect, the dose of medroxyprogesterone is 2.5 mg or 5 mg. In yet another aspect, the medroxyprogesterone is administered once a day.

In still yet another aspect of the invention, the progestogen is drospirenone. In another aspect, the dose of drospirenone is 0.25 mg. In still yet another aspect, the dose of drospirenone is 0.5 mg. In yet another aspect, the drospirenone is administered once a day.

In one aspect of the invention, the dose of Elagolix is 300 mg administered twice a day in combination with 0.5 mg estradiol and 0.1 mg norethindrone acetate.

In yet another aspect of the invention, the dose of Elagolix is 300 mg administered once or twice a day in combination with 1.0 mg estradiol and 0.5 mg norethindrone acetate.

In still yet another aspect of the invention, the dose of Elagolix is 400 mg administered once or twice a day in combination with 0.5 mg estradiol and 0.1 mg norethindrone acetate.

In still yet another aspect of the invention, the dose of Elagolix is 400 mg administered once or twice a day in combination with 1.0 mg estradiol and 0.5 mg norethindrone acetate.

In still yet another aspect of the invention, the dose of Elagolix is 600 mg administered once or twice a day in combination with 0.5 mg estradiol and 0.1 mg norethindrone acetate.

In still yet another aspect of the invention, the dose of Elagolix is 600 mg administered once or twice a day in combination with 1.0 mg estradiol and 0.5 mg norethindrone acetate.

The administration of Elagolix or a pharmaceutically acceptable salt or solvate thereof, and compositions and formulations thereof, may be prior to, immediately prior to, during, immediately subsequent to or subsequent to the administration of the estrogens and progestogens.

In still yet another aspect, the treatment cycle consist of daily administration of Elagolix and cyclical administration of progestogens in combination with a continuously administered estrogen. For example, the treatment cycle is 3 months or 6 months of daily administration of Elagolix and estrogens and progestogens are administered for the last 12-14 days of each month in order to mimic the normal menstrual cycle and induce regular, light bleeding episodes. In still yet another aspect, the treatment cycle consist of daily administration of Elagolix and estrogens and cyclical administration of progestogens.

In still yet a further aspect, the treatment cycle consist of daily administration of Elagolix and delayed administration of estrogens and/or progestogens. For example, the treatment cycle is 6 months of daily administration of Elagolix while estrogens and progestogens are administered daily for months 3-6. Alternatively, the treatment cycle is 12 months of daily administration of Elagolix while estrogens and progestogens are administered daily for months 3-12.

Methods of Reducing Fibroid Volume in a Subject with Uterine Fibroids

In another embodiment, the present invention relates to methods for reducing the fibroid volume in a subject with uterine fibroids. In one aspect, the methods of the present invention can be used to reduce the fibroid volume by greater than or equal to at least about 25%. In another aspect, the methods of the present invention can be used to reduce the fibroid volume in a subject with uterine fibroids. More specifically, the methods of the present invention can be used to reduce the fibroid volume in a subject with uterine fibroids by volume by greater than or equal to at least about 25%. In another aspect, the methods of the present invention are used to reduce the fibroid volume in a subject with uterine fibroids prior to hysterectomy, myomectomy, or uterine artery embolization. Methods for measuring fibroid volume are known in the art and include ultrasound and/or MRI.

a. Use of Elagolix or a Pharmaceutically Acceptable Salt Thereof

In one aspect, the methods of the present invention involve reducing the fibroid volume in a subject with uterine fibroids and in need of treatment thereof. The methods involve administering to a subject suffering with uterine fibroids an effective amount of Elagolix or a pharmaceutically acceptable salt thereof. The effective amount or dose of Elagolix or a pharmaceutically acceptable salt thereof that can be administered to a subject is in the range of 300 to 600 mg per day. In a further aspect of the invention, the effective amount or dose of Elagolix or a pharmaceutically acceptable salt or solvate thereof is about 300 mg, 400 mg, or 600 mg per day. In still yet another aspect of the invention, the effective amount or dose of Elagolix or a pharmaceutically acceptable salt or solvate thereof is about 300 mg per day. In still yet another aspect of the invention, the effective amount or dose of Elagolix or a pharmaceutically acceptable salt or solvate thereof is about 400 mg per day. In still yet another aspect of the invention, the effective amount or dose of Elagolix or a pharmaceutically acceptable salt or solvate thereof is about 600 mg per day. The dose can be administered once a day or twice a day.

b. Use of Elagolix or a Pharmaceutically Acceptable Salt Thereof in Combination with Hormone Replacement Therapy In another aspect, the methods of the present invention involve reducing the total fibroid volume in a subject with uterine fibroids and in need of treatment thereof. The methods involve administering to a subject suffering with uterine fibroids an effective amount of Elagolix or a pharmaceutically acceptable salt thereof in combination with one or more estrogens and progestogens. The methods involve administering to a subject suffering from heavy menstrual bleeding associated with uterine fibroids an effective amount of Elagolix or a pharmaceutically acceptable salt thereof in combination with estrogens and progestogens.

The effective amount or dose of Elagolix or a pharmaceutically acceptable salt thereof that can be administered to a subject is in the range of 300 to 600 mg per day. In a further aspect of the invention, the effective amount or dose of Elagolix or a pharmaceutically acceptable salt or solvate thereof is about 300 mg, 400 mg, or 600 mg per day. In still yet another aspect of the invention, the effective amount or dose of Elagolix or a pharmaceutically acceptable salt or solvate thereof is about 300 mg per day. In still yet another aspect of the invention, the effective amount or dose of Elagolix or a pharmaceutically acceptable salt or solvate thereof is about 400 mg per day. In still yet another aspect of the invention, the effective amount or dose of Elagolix or a pharmaceutically acceptable salt or solvate thereof is about 600 mg per day. The effective amount or dose can be administered once a day or twice a day. The estrogen and/or progestogens can be administered orally, transdermally or intravaginally.

Suitable estrogens that can be used include, for example, estradiol, ethinyl estradiol, and conjugated estrogens.

Suitable progestogens that can be used include, for example, progesterone, norethindrone, norethindrone acetate, norgestimate, drospirenone, and medroxyprogestogen.

Combined formulations, used continuously, containing estogens and progestogens for hormone replacement therapy are known in the art and can also be used in the invention. Suitable formulations include, for example, Activella®, Angeliq®, FemHRT®, Jenteli™ Mimvey™, Prefest™, Premphase®, and Prempro®.

In one aspect of the invention, the estrogen is estradiol. In another aspect, the dose of estradiol is 0.5 mg. In another embodiment, the dose of estradiol is 1.0 mg. In yet another embodiment, the estradiol is administered once a day.

In another aspect of the invention, the estrogen is ethinyl estradiol. In another embodiment, the dose of ethinyl estradiol is 2.5 mcg. In yet another embodiment, the dose of estradiol is 5.0 mcg. In still yet another aspect, the ethinyl estradiol is administered once a day.

In still yet another aspect of the invention, the estrogen is conjugated estrogens. In another embodiment, the dose of conjugated estrogens is 0.3 mg. In still yet another embodiment, the dose of conjugated estrogens is 0.45 mg or 0.625 mg. In still yet another embodiment, the conjugated estrogens is administered once a day.

In still yet another aspect of the invention, the progestogen is progesterone, which is used cyclically (for the last 12 days of the 28-30 day cycle). In another embodiment, the dose of progesterone is 100 or 200 mg.

In still yet another aspect of the invention, the progestogen is norethindrone or norethindrone acetate. In another aspect, the dose of norethindrone or norethindrone acetate is 0.1 mg. In another aspect, the dose of norethindrone or norethindrone acetate is 0.5 mg. In another embodiment, the dose of norethindrone or norethindrone acetate is 1.0 mg. In yet another aspect, the norethindrone or norethindrone acetate is administered once a day.

In still yet another aspect of the invention, the progestogen is norgestimate. In another aspect, the dose of norgestimate is 0.09 mg. In still yet another aspect, the norgestimate is administered once a day.

In still yet another aspect of the invention, the progestogen is medroxyprogesterone. In still yet another aspect of the invention, the dose of medroxyprogesterone is 1.5 mg. In another aspect, the dose of medroxyprogesterone is 2.5 mg or 5 mg. In yet another aspect, the medroxyprogesterone is administered once a day.

In still yet another aspect of the invention, the progestogen is drospirenone. In another aspect, the dose of drospirenone is 0.25 mg. In still yet another aspect, the dose of drospirenone is 0.5 mg. In yet another aspect, the drospirenone is administered once a day.

In one aspect of the invention, the dose of Elagolix is 300 mg administered twice a day in combination with 0.5 mg estradiol and 0.1 mg norethindrone acetate.

In yet another aspect of the invention, the dose of Elagolix is 300 mg administered once or twice a day in combination with 1.0 mg estradiol and 0.5 mg norethindrone acetate.

In still yet another aspect of the invention, the dose of Elagolix is 400 mg administered once or twice a day in combination with 0.5 mg estradiol and 0.1 mg norethindrone acetate.

In still yet another aspect of the invention, the dose of Elagolix is 400 mg administered once or twice a day in combination with 1.0 mg estradiol and 0.5 mg norethindrone acetate.

In still yet another aspect of the invention, the dose of Elagolix is 600 mg administered once or twice a day in combination with 0.5 mg estradiol and 0.1 mg norethindrone acetate.

In still yet another aspect of the invention, the dose of Elagolix is 600 mg administered once or twice a day in combination with 1.0 mg estradiol and 0.5 mg norethindrone acetate.

The administration of Elagolix or a pharmaceutically acceptable salt or solvate thereof, and compositions and formulations thereof, may be prior to, immediately prior to, during, immediately subsequent to or subsequent to the administration of the estrogens and progestogens.

In still yet another aspect, the treatment cycle consist of daily administration of Elagolix and cyclical administration of progestogens in combination with a continuously administered estrogen. For example, the treatment cycle is 3 months or 6 months of daily administration of Elagolix and estrogens and progestogens are administered for the last 12-14 days of each month in order to mimic the normal menstrual cycle and induce regular, light bleeding episodes. In still yet another aspect, the treatment cycle consist of daily administration of Elagolix and estrogens and cyclical administration of progestogens.

In still yet a further aspect, the treatment cycle consist of daily administration of Elagolix and delayed administration of estrogens and/or progestogens. For example, the treatment cycle is 6 months of daily administration of Elagolix while estrogens and progestogens are administered daily for months 3-6. Alternatively, the treatment cycle is 12 months of daily administration of Elagolix while estrogens and progestogens are administered daily for months 3-12.

Methods of Reducing Total Uterine Volume in a Subject with Uterine Fibroids

In another embodiment, the present invention relates to methods for reducing the total uterine volume in a subject with uterine fibroids. The "total uterine volume" is the volume of the entire uterus. In one aspect, the methods of the present invention can be used to reduce the total uterine volume by greater than or equal to at least about 25%. In another aspect, the methods of the present invention can be used to reduce the total uterine volume in a subject with uterine fibroids. More specifically, the methods of the present invention can be used to reduce the total uterine volume in a subject with uterine fibroids by greater than or equal to at least about 25%. Methods for measuring total uterine volume are known in the art and include, ultrasound and/or MRI.

a. Use of Elagolix or a Pharmaceutically Acceptable Salt Thereof

In one aspect, the methods of the present invention involve reducing the total uterine volume in a subject with uterine fibroids and in need of treatment thereof. The methods involve administering to a subject suffering with uterine fibroids an effective amount of Elagolix or a pharmaceutically acceptable salt thereof. The effective amount or dose of Elagolix or a pharmaceutically acceptable salt thereof that can be administered to a subject is in the range of 300 to 600 mg per day. In a further aspect of the invention, the effective amount or dose of Elagolix or a pharmaceutically acceptable salt or solvate thereof is about 300 mg, 400 mg, or 600 mg per day. In still yet another aspect of the invention, the effective amount or dose of Elagolix or a pharmaceutically acceptable salt or solvate thereof is about 300 mg per day. In still yet another aspect of the invention, the effective amount or dose of Elagolix or a pharmaceutically acceptable salt or solvate thereof is about 400 mg per day. In still yet another aspect of the invention, the effective amount or dose of Elagolix or a pharmaceutically acceptable salt or solvate thereof is about 600 mg per day. The dose can be administered once a day or twice a day.

b. Use of Elagolix or a Pharmaceutically Acceptable Salt Thereof in Combination with Hormone Replacement Therapy In another aspect, the methods of the present invention involve reducing the uterine volume in a subject with uterine fibroids and in need of treatment thereof. The methods involve administering to a subject suffering with uterine fibroids an effective amount of Elagolix or a pharmaceutically acceptable salt thereof in combination with one or more estrogens and progestogens. The methods involve administering to a subject suffering from heavy menstrual bleeding associated with uterine fibroids an effective amount of Elagolix or a pharmaceutically acceptable salt thereof in combination with one or more estrogens and progestogens.

The effective amount or dose of Elagolix or a pharmaceutically acceptable salt thereof that can be administered to a subject is in the range of 300 to 600 mg per day. In a further aspect of the invention, the effective amount or dose of Elagolix or a pharmaceutically acceptable salt or solvate thereof is about 300 mg, 400 mg, or 600 mg per day. In still yet another aspect of the invention, the effective amount or dose of Elagolix or a pharmaceutically acceptable salt or solvate thereof is about 300 mg per day. In still yet another aspect of the invention, the effective amount or dose of Elagolix or a pharmaceutically acceptable salt or solvate thereof is about 400 mg per day. In still yet another aspect of the invention, the effective amount or dose of Elagolix or a pharmaceutically acceptable salt or solvate thereof is about 600 mg per day. The effective amount or dose can be administered once a day or twice a day. The estrogen and/or progestogens can be administered orally, transdermally or intravaginally.

Suitable estrogens that can be used include, for example, estradiol, ethinyl estradiol, and conjugated estrogens.

Suitable progestogens that can be used include, for example, progesterone, norethindrone, norethindrone acetate, norgestimate, drospirenone, and medroxyprogestogen.

Combined formulations, used continuously, containing estogens and progestogens for hormone replacement therapy are known in the art and can also be used in the invention. Suitable formulations include, for example, Activella®, Angeliq®, FemHRT®, Jenteli™ Mimvey™, Prefest™, Premphase®, and Prempro®.

In one aspect of the invention, the estrogen is estradiol. In another aspect, the dose of estradiol is 0.5 mg. In another embodiment, the dose of estradiol is 1.0 mg. In yet another embodiment, the estradiol is administered once a day.

In another aspect of the invention, the estrogen is ethinyl estradiol. In another embodiment, the dose of ethinyl estradiol is 2.5 mcg. In yet another embodiment, the dose of estradiol is 5.0 mcg. In still yet another aspect, the ethinyl estradiol is administered once a day.

In still yet another aspect of the invention, the estrogen is conjugated estrogens. In another embodiment, the dose of conjugated estrogens is 0.3 mg. In still yet another embodiment, the dose of conjugated estrogens is 0.45 mg or 0.625 mg. In still yet another embodiment, the conjugated estrogens is administered once a day.

In still yet another aspect of the invention, the progestogen is progesterone, which is used cyclically (for the last 12 days of the 28-30 day cycle). In another embodiment, the dose of progesterone is 100 or 200 mg.

In still yet another aspect of the invention, the progestogen is norethindrone or norethindrone acetate. In another aspect, the dose of norethindrone or norethindrone acetate is 0.1 mg. In another aspect, the dose of norethindrone or norethindrone acetate is 0.5 mg. In another embodiment, the dose of norethindrone or norethindrone acetate is 1.0 mg. In yet another aspect, the norethindrone or norethindrone acetate is administered once a day.

In still yet another aspect of the invention, the progestogen is norgestimate. In another aspect, the dose of norgestimate is 0.09 mg. In still yet another aspect, the norgestimate is administered once a day.

In still yet another aspect of the invention, the progestogen is medroxyprogesterone. In still yet another aspect of the invention, the dose of medroxyprogesterone is 1.5 mg. In another aspect, the dose of medroxyprogesterone is 2.5 mg or 5 mg. In yet another aspect, the medroxyprogesterone is administered once a day.

In still yet another aspect of the invention, the progestogen is drospirenone. In another aspect, the dose of drospirenone is 0.25 mg. In still yet another aspect, the dose of drospirenone is 0.5 mg. In yet another aspect, the drospirenone is administered once a day.

In one aspect of the invention, the dose of Elagolix is 300 mg administered twice a day in combination with 0.5 mg estradiol and 0.1 mg norethindrone acetate.

In yet another aspect of the invention, the dose of Elagolix is 300 mg administered once or twice a day in combination with 1.0 mg estradiol and 0.5 mg norethindrone acetate.

In still yet another aspect of the invention, the dose of Elagolix is 400 mg administered once or twice a day in combination with 0.5 mg estradiol and 0.1 mg norethindrone acetate.

In still yet another aspect of the invention, the dose of Elagolix is 400 mg administered once or twice a day in combination with 1.0 mg estradiol and 0.5 mg norethindrone acetate.

In still yet another aspect of the invention, the dose of Elagolix is 600 mg administered once or twice a day in combination with 0.5 mg estradiol and 0.1 mg norethindrone acetate.

In still yet another aspect of the invention, the dose of Elagolix is 600 mg administered once or twice a day in combination with 1.0 mg estradiol and 0.5 mg norethindrone acetate.

The administration of Elagolix or a pharmaceutically acceptable salt or solvate thereof, and compositions and formulations thereof, may be prior to, immediately prior to, during, immediately subsequent to or subsequent to the administration of the estrogens and progestogens.

In still yet another aspect, the treatment cycle consist of daily administration of Elagolix and cyclical administration of progestogens in combination with a continuously administered estrogen. For example, the treatment cycle is 3 months or 6 months of daily administration of Elagolix and estrogens and progestogens are administered for the last 12-14 days of each month in order to mimic the normal menstrual cycle and induce regular, light bleeding episodes. In still yet another aspect, the treatment cycle consist of daily administration of Elagolix and estrogens and cyclical administration of progestogens.

In still yet a further aspect, the treatment cycle consist of daily administration of Elagolix and delayed administration of estrogens and/or progestogens. For example, the treatment cycle is 6 months of daily administration of Elagolix while estrogens and progestogens are administered daily for months 3-6. Alternatively, the treatment cycle is 12 months of daily administration of Elagolix while estrogens and progestogens are administered daily for months 3-12.

Methods of Preventing Uterine Fibroid Regrowth or Recurrence after Surgical or Semi-Invasive Intervention In still yet another embodiment, the present invention relates to methods for preventing the regrowth or recurrence of uterine fibroids in a subject after removal of one or more uterine fibroids from the subject by surgical (such as myomectomy) or semi-invasive intervention (such as uterine artery embolization, MRI-guided high-intensity focused ultrasound, etc).

a. Use of Elagolix or a Pharmaceutically Acceptable Salt Thereof

In one aspect, the methods of the present invention involve preventing the regrowth or return of uterine fibroids in a subject after removal of one or more uterine fibroids from the subject by surgical or semi-invasive intervention. The methods involve administering to a subject who has had one or more uterine fibroids removed (such as by surgical or semi-invasive intervention) an effective amount of Elagolix or a pharmaceutically acceptable salt thereof The Elagolix or pharmaceutically acceptable salt thereof can be administered to a subject in need thereof immediately after surgery "Immediately after surgery" refers to administration of the Elagolix or pharmaceutically acceptable salt thereof 1 day post surgery, 2 days post surgery, 3 days post surgery, 4 days post surgery, 5 days post surgery, 6 days post surgery or 7 days post surgery. The Elagolix or pharmaceutically acceptable salt thereof can be administered to a subject daily (namely, continuously), post-surgery for a duration of at least 6 months, at least 12 months, at least 18 months, at least 24 months, etc. The effective amount or dose of Elagolix or a pharmaceutically acceptable salt thereof that can be administered to a subject is in the range of 300 to 600 mg per day. In a further aspect of the invention, the effective amount or dose of Elagolix or a pharmaceutically acceptable salt or solvate thereof is about 300 mg, 400 mg, or 600 mg per day. In still yet another aspect of the invention, the effective amount or dose of Elagolix or a pharmaceutically acceptable salt or solvate thereof is about 300 mg per day. In still yet another aspect of the invention, the effective amount or dose of Elagolix or a pharmaceutically acceptable salt or solvate thereof is about 400 mg per day. In still yet another aspect of the invention, the effective amount or dose of Elagolix or a pharmaceutically acceptable salt or solvate thereof is about 600 mg per day. The dose can be administered once a day or twice a day.

b. Use of Elagolix or a Pharmaceutically Acceptable Salt Thereof in Combination with Hormone Replacement Therapy In still yet another aspect, the methods of the present invention involve preventing the regrowth or recurrence of uterine fibroids in a subject after removal of one or more uterine fibroids from the subject by surgical or semi-invasive intervention. The methods involve administering to a subject who has had one or more uterine fibroids removed (such as by surgical or semi-invasive intervention) an effective amount of Elagolix or a pharmaceutically acceptable salt thereof in combination with one or more estrogens and progestogens.

The Elagolix or pharmaceutically acceptable salt thereof in combination with one or more estrogens and progestogens can be administered to a subject in need thereof immediately after surgery "Immediately after surgery" refers to administration of the Elagolix or pharmaceutically acceptable salt thereof 1 day post surgery, 2 days post surgery, 3 days post surgery, 4 days post surgery, 5 days post surgery, 6 days post surgery or 7 days post surgery. The Elagolix or pharmaceutically acceptable salt thereof can be administered to a subject daily (namely, continuously), post-surgery for a duration of at least 6 months, at least 12 months, at least 18 months, at least 24 months, etc.

The effective amount or dose of Elagolix or a pharmaceutically acceptable salt thereof that can be administered to a subject is in the range of 300 to 600 mg per day. In a further aspect of the invention, the effective amount or dose of Elagolix or a pharmaceutically acceptable salt or solvate thereof is about 300 mg, 400 mg, or 600 mg per day. In still yet another aspect of the invention, the effective amount or dose of Elagolix or a pharmaceutically acceptable salt or solvate thereof is about 300 mg per day. In still yet another aspect of the invention, the effective amount or dose of Elagolix or a pharmaceutically acceptable salt or solvate thereof is about 400 mg per day. In still yet another aspect of the invention, the effective amount or dose of Elagolix or a pharmaceutically acceptable salt or solvate thereof is about 600 mg per day. The effective amount or dose can be administered once a day or twice a day. The estrogen and/or progestogens can be administered orally, transdermally or intravaginally.

Suitable estrogens that can be used include, for example, estradiol, ethinyl estradiol, and conjugated estrogens.

Suitable progestogens that can be used include, for example, progesterone, norethindrone, norethindrone acetate, norgestimate, drospirenone, and medroxyprogestogen.

Combined formulations, used continuously, containing estogens and progestogens for hormone replacement therapy are known in the art and can also be used in the invention. Suitable formulations include, for example, Activella®, Angeliq®, FemHRT®, Jenteli™, Mimvey™, Prefest™, Premphase®, and Prempro®.

In one aspect of the invention, the estrogen is estradiol. In another aspect, the dose of estradiol is 0.5 mg. In another embodiment, the dose of estradiol is 1.0 mg. In yet another embodiment, the estradiol is administered once a day.

In another aspect of the invention, the estrogen is ethinyl estradiol. In another embodiment, the dose of ethinyl estradiol is 2.5 mcg. In yet another embodiment, the dose of estradiol is 5.0 mcg. In still yet another aspect, the ethinyl estradiol is administered once a day.

In still yet another aspect of the invention, the estrogen is conjugated estrogens. In another embodiment, the dose of conjugated estrogens is 0.3 mg. In still yet another embodiment, the dose of conjugated estrogens is 0.45 mg or 0.625 mg. In still yet another embodiment, the conjugated estrogens is administered once a day.

In still yet another aspect of the invention, the progestogen is progesterone, which is used cyclically (for the last 12 days of the 28-30 day cycle). In another embodiment, the dose of progesterone is 100 or 200 mg.

In still yet another aspect of the invention, the progestogen is norethindrone or norethindrone acetate. In another aspect, the dose of norethindrone or norethindrone acetate is 0.1 mg. In another aspect, the dose of norethindrone or norethindrone acetate is 0.5 mg. In another embodiment, the dose of norethindrone or norethindrone acetate is 1.0 mg. In yet another aspect, the norethindrone or norethindrone acetate is administered once a day.

In still yet another aspect of the invention, the progestogen is norgestimate. In another aspect, the dose of norgestimate is 0.09 mg. In still yet another aspect, the norgestimate is administered once a day.

In still yet another aspect of the invention, the progestogen is medroxyprogesterone. In still yet another aspect of the invention, the dose of medroxyprogesterone is 1.5 mg. In another aspect, the dose of medroxyprogesterone is 2.5 mg or 5 mg. In yet another aspect, the medroxyprogesterone is administered once a day.

In still yet another aspect of the invention, the progestogen is drospirenone. In another aspect, the dose of drospirenone is 0.25 mg. In still yet another aspect, the dose of drospirenone is 0.5 mg. In yet another aspect, the drospirenone is administered once a day.

In one aspect of the invention, the dose of Elagolix is 300 mg administered twice a day in combination with 0.5 mg estradiol and 0.1 mg norethindrone acetate.

In yet another aspect of the invention, the dose of Elagolix is 300 mg administered once or twice a day in combination with 1.0 mg estradiol and 0.5 mg norethindrone acetate.

In still yet another aspect of the invention, the dose of Elagolix is 400 mg administered once or twice a day in combination with 0.5 mg estradiol and 0.1 mg norethindrone acetate.

In still yet another aspect of the invention, the dose of Elagolix is 400 mg administered once or twice a day in combination with 1.0 mg estradiol and 0.5 mg norethindrone acetate.

In still yet another aspect of the invention, the dose of Elagolix is 600 mg administered once or twice a day in combination with 0.5 mg estradiol and 0.1 mg norethindrone acetate.

In still yet another aspect of the invention, the dose of Elagolix is 600 mg administered once or twice a day in combination with 1.0 mg estradiol and 0.5 mg norethindrone acetate.

The administration of Elagolix or a pharmaceutically acceptable salt or solvate thereof, and compositions and formulations thereof, may be prior to, immediately prior to, during, immediately subsequent to or subsequent to the administration of the estrogens and progestogens.

In still yet another aspect, the treatment cycle consist of daily administration of Elagolix and cyclical administration of progestogens in combination with a continuously administered estrogen. For example, the treatment cycle is 3 months or 6 months of daily administration of Elagolix and estrogens and progestogens are administered for the last 12-14 days of each month in order to mimic the normal menstrual cycle and induce regular, light bleeding episodes. In still yet another aspect, the treatment cycle consist of daily administration of Elagolix and estrogens and cyclical administration of progestogens.

In still yet a further aspect, the treatment cycle consist of daily administration of Elagolix and delayed administration of estrogens and/or progestogens. For example, the treatment cycle is 6 months of daily administration of Elagolix while estrogens and progestogens are administered daily for months 3-6. Alternatively, the treatment cycle is 12 months of daily administration of Elagolix while estrogens and progestogens are administered daily for months 3-12.

Methods of Reducing or Managing Heavy Menstrual Bleeding not Associated with Uterine Fibroids In one embodiment, the present invention relates to methods for reducing or managing heavy menstrual bleeding (HMB) in subjects in need of treatment thereof where the heavy menstrual bleeding is not associated with uterine fibroids but is the result of other conditions, such as adenomyosis, hereditary bleeding disorders, idiopathic heavy menstrual bleeding, etc. In one aspect, the methods of the present invention can be used to reduce or manage heavy menstrual bleeding to less than 80 mL of blood loss per cycle. In another aspect, the methods of the present invention can be used to reduce the volume of heavy menstrual bleeding in the subject by 50% from baseline.

a. Use of Elagolix or a Pharmaceutically Acceptable Salt Thereof

In one aspect, the methods of the present invention involve reducing or managing heavy menstrual bleeding associated with conditions other than uterine fibroids in a subject in need of treatment thereof. The methods involve administering to a subject suffering from heavy menstrual bleeding associated with conditions other than uterine fibroids an effective amount of Elagolix or a pharmaceutically acceptable salt thereof. In one aspect, the subject may not have any uterine fibroids. In another aspect, the subject may have uterine fibroids but the heavy menstrual bleeding is not a result of the uterine fibroids.

The effective amount or dose of Elagolix or a pharmaceutically acceptable salt thereof that can be administered to a subject is in the range of 300 to 600 mg per day. In a further aspect of the invention, the effective amount or dose of Elagolix or a pharmaceutically acceptable salt or solvate thereof is about 300 mg, 400 mg, or 600 mg per day. In still yet another aspect of the invention, the effective amount or dose of Elagolix or a pharmaceutically acceptable salt or solvate thereof is about 300 mg per day. In still yet another aspect of the invention, the effective amount or dose of Elagolix or a pharmaceutically acceptable salt or solvate thereof is about 400 mg per day. In still yet another aspect of the invention, the effective amount or dose of Elagolix or a pharmaceutically acceptable salt or solvate thereof is about 600 mg per day. The dose can be administered once a day or twice a day. The estrogen and/or progestogens can be administered orally, transdermally or intravaginally.

b. Use of Elagolix or a Pharmaceutically Acceptable Salt Thereof in Combination with Hormone Replacement Therapy In another aspect, the methods of the present invention involve reducing or managing heavy menstrual bleeding associated with conditions other than uterine fibroids in a subject in need of treatment thereof. The methods involve administering to a subject suffering from heavy menstrual bleeding associated with conditions other than uterine fibroids an effective amount of Elagolix or a pharmaceutically acceptable salt thereof in combination with one or more estrogens and progestogens. The methods involve administering to a subject suffering from heavy menstrual bleeding associated with uterine fibroids an effective amount of Elagolix or a pharmaceutically acceptable salt thereof in combination with estrogens and progestogens. In one aspect, the subject may not have any uterine fibroids. In another aspect, the subject may have uterine fibroids but the heavy menstrual bleeding is not a result of the uterine fibroids.

The effective amount or dose of Elagolix or a pharmaceutically acceptable salt thereof that can be administered to a subject is in the range of 300 to 600 mg per day. In a further aspect of the invention, the effective amount or dose of Elagolix or a pharmaceutically acceptable salt or solvate thereof is about 300 mg, 400 mg, or 600 mg per day. In still yet another aspect of the invention, the effective amount or dose of Elagolix or a pharmaceutically acceptable salt or solvate thereof is about 300 mg per day. In still yet another aspect of the invention, the effective amount or dose of Elagolix or a pharmaceutically acceptable salt or solvate thereof is about 400 mg per day. In still yet another aspect of the invention, the effective amount or dose of Elagolix or a pharmaceutically acceptable salt or solvate thereof is about 600 mg per day. The effective amount or dose can be administered once a day or twice a day. The estrogen and/or progestogens can be administered orally, transdermally or intravaginally.

Suitable estrogens that can be used include, for example, estradiol, ethinyl estradiol, and conjugated estrogens.

Suitable progestogens that can be used include, for example, progesterone, norethindrone, norethindrone acetate, norgestimate, drospirenone, and medroxyprogestogen.

Combined formulations, used continuously, containing estogens and progestogens for hormone replacement therapy are known in the art and can also be used in the invention. Suitable formulations include, for example, Activella®, Angeliq®, FemHRT®, Jenteli™ Mimvey™, Prefest™, Premphase®, and Prempro®.

In one aspect of the invention, the estrogen is estradiol. In another aspect, the dose of estradiol is 0.5 mg. In another embodiment, the dose of estradiol is 1.0 mg. In yet another embodiment, the estradiol is administered once a day.

In another aspect of the invention, the estrogen is ethinyl estradiol. In another embodiment, the dose of ethinyl estradiol is 2.5 mcg. In yet another embodiment, the dose of estradiol is 5.0 mcg. In still yet another aspect, the ethinyl estradiol is administered once a day.

In still yet another aspect of the invention, the estrogen is conjugated estrogens. In another embodiment, the dose of conjugated estrogens is 0.3 mg. In still yet another embodiment, the dose of conjugated estrogens is 0.45 mg or 0.625 mg. In still yet another embodiment, the conjugated estrogens is administered once a day.

In still yet another aspect of the invention, the progestogen is progesterone, which is used cyclically (for the last 12 days of the 28-30 day cycle). In another embodiment, the dose of progesterone is 100 or 200 mg.

In still yet another aspect of the invention, the progestogen is norethindrone or norethindrone acetate. In another aspect, the dose of norethindrone or norethindrone acetate is 0.1 mg. In another aspect, the dose of norethindrone or norethindrone acetate is 0.5 mg. In another embodiment, the dose of norethindrone or norethindrone acetate is 1.0 mg. In yet another aspect, the norethindrone or norethindrone acetate is administered once a day.

In still yet another aspect of the invention, the progestogen is norgestimate. In another aspect, the dose of norgestimate is 0.09 mg. In still yet another aspect, the norgestimate is administered once a day.

In still yet another aspect of the invention, the progestogen is medroxyprogesterone. In still yet another aspect of the invention, the dose of medroxyprogesterone is 1.5 mg. In another aspect, the dose of medroxyprogesterone is 2.5 mg or 5 mg. In yet another aspect, the medroxyprogesterone is administered once a day.

In still yet another aspect of the invention, the progestogen is drospirenone. In another aspect, the dose of drospirenone is 0.25 mg. In still yet another aspect, the dose of drospirenone is 0.5 mg. In yet another aspect, the drospirenone is administered once a day.

In one aspect of the invention, the dose of Elagolix is 300 mg administered twice a day in combination with 0.5 mg estradiol and 0.1 mg norethindrone acetate.

In yet another aspect of the invention, the dose of Elagolix is 300 mg administered once or twice a day in combination with 1.0 mg estradiol and 0.5 mg norethindrone acetate.

In still yet another aspect of the invention, the dose of Elagolix is 400 mg administered once or twice a day in combination with 0.5 mg estradiol and 0.1 mg norethindrone acetate.

In still yet another aspect of the invention, the dose of Elagolix is 400 mg administered once or twice a day in combination with 1.0 mg estradiol and 0.5 mg norethindrone acetate.

In still yet another aspect of the invention, the dose of Elagolix is 600 mg administered once or twice a day in combination with 0.5 mg estradiol and 0.1 mg norethindrone acetate.

In still yet another aspect of the invention, the dose of Elagolix is 600 mg administered once or twice a day in combination with 1.0 mg estradiol and 0.5 mg norethindrone acetate.

The administration of Elagolix or a pharmaceutically acceptable salt or solvate thereof, and compositions and formulations thereof, may be prior to, immediately prior to, during, immediately subsequent to or subsequent to the administration of the estrogens and progestogens.

In still yet another aspect, the treatment cycle consist of daily administration of Elagolix and cyclical administration of progestogens in combination with a continuously administered estrogen. For example, the treatment cycle is 3 months or 6 months of daily administration of Elagolix and estrogens and progestogens are administered for the last 12-14 days of each month in order to mimic the normal menstrual cycle and induce regular, light bleeding episodes. In still yet another aspect, the treatment cycle consist of daily administration of Elagolix and estrogens and cyclical administration of progestogens.

In still yet a further aspect, the treatment cycle consist of daily administration of Elagolix and delayed administration of estrogens and/or progestogens. For example, the treatment cycle is 6 months of daily administration of Elagolix while estrogens and progestogens are administered daily for months 3-6. Alternatively, the treatment cycle is 12 months of daily administration of Elagolix while estrogens and progestogens are administered daily for months 3-12.

Methods of Treating Uterine Fibroids in Subjects in Need of Treatment Thereof

In one embodiment, the present invention relates to methods for treating subjects having uterine fibroids and in need of treatment thereof. Subjects having uterine fibroids and treated pursuant to this method may not experience heavy menstrual bleeding but instead exhibit other uterine fibroid symptoms such as pelvic pressure, pelvic pain, bloating, urinary symptoms, etc.

a. Use of Elagolix or a Pharmaceutically Acceptable Salt Thereof

In one aspect, the methods of the present invention involve treating subjects having uterine fibroids that do not exhibit heavy menstrual bleeding but are in need of treatment thereof. The methods involve administering to a subject having uterine fibroids (and that does not exhibit heavy menstrual bleeding) an effective amount of Elagolix or a pharmaceutically acceptable salt thereof. The effective amount or dose of Elagolix or a pharmaceutically acceptable salt thereof that can be administered to a subject is in the range 300 to 600 mg per day. In a further aspect of the invention, the effective amount or dose of Elagolix or a pharmaceutically acceptable salt or solvate thereof is about 300 mg, 400 mg, or 600 mg per day. In still yet another aspect of the invention, the effective amount or dose of Elagolix or a pharmaceutically acceptable salt or solvate thereof is about 300 mg per day. In still yet another aspect of the invention, the effective amount or dose of Elagolix or a pharmaceutically acceptable salt or solvate thereof is about 400 mg per day. In still yet another aspect of the invention, the effective amount or dose of Elagolix or a pharmaceutically acceptable salt or solvate thereof is about 600 mg per day. The dose can be administered once a day or twice a day. The estrogen and/or progestogens can be administered orally, transdermally or intravaginally.

b. Use of Elagolix or a Pharmaceutically Acceptable Salt Thereof in Combination with Hormone Replacement Therapy In another aspect, the methods of the present invention treating a subject uterine fibroids in a subject in need of treatment thereof. The methods involve administering to a subject having uterine fibroids (and that does not exhibit heavy menstrual bleeding) an effective amount of Elagolix or a pharmaceutically acceptable salt thereof in combination with estrogens and progestogens. The methods involve administering to a subject suffering from uterine fibroids (and that does not exhibit heavy menstrual bleeding) an effective amount of Elagolix or a pharmaceutically acceptable salt thereof in combination with one or more estrogens and progestogens.

The effective amount or dose of Elagolix or a pharmaceutically acceptable salt thereof that can be administered to a subject is in the range of 300 to 600 mg per day. In a further aspect of the invention, the effective amount or dose of Elagolix or a pharmaceutically acceptable salt or solvate thereof is about 300 mg, 400 mg, or 600 mg per day. In still yet another aspect of the invention, the effective amount or dose of Elagolix or a pharmaceutically acceptable salt or solvate thereof is about 300 mg per day. In still yet another aspect of the invention, the effective amount or dose of Elagolix or a pharmaceutically acceptable salt or solvate thereof is about 400 mg per day. In still yet another aspect of the invention, the effective amount or dose of Elagolix or a pharmaceutically acceptable salt or solvate thereof is about 600 mg per day. The effective amount or dose can be administered once a day or twice a day. The estrogen and/or progestogens can be administered orally, transdermally or intravaginally.

Suitable estrogens that can be used include, for example, estradiol, ethinyl estradiol, and conjugated estrogens.

Suitable progestogens that can be used include, for example, progesterone, norethindrone, norethindrone acetate, norgestimate, drospirenone, and medroxyprogestogen.

Combined formulations, used continuously, containing estogens and progestogens for hormone replacement therapy are known in the art and can also be used in the invention. Suitable formulations include, for example, Activella®, Angeliq®, FemHRT®, Jenteli™ Mimvey™, Prefest™, Premphase®, and Prempro®.

In one aspect of the invention, the estrogen is estradiol. In another aspect, the dose of estradiol is 0.5 mg. In another embodiment, the dose of estradiol is 1.0 mg. In yet another embodiment, the estradiol is administered once a day.

In another aspect of the invention, the estrogen is ethinyl estradiol. In another embodiment, the dose of ethinyl estradiol is 2.5 mcg. In yet another embodiment, the dose of estradiol is 5.0 mcg. In still yet another aspect, the ethinyl estradiol is administered once a day.

In still yet another aspect of the invention, the estrogen is conjugated estrogens. In another embodiment, the dose of conjugated estrogens is 0.3 mg. In still yet another embodiment, the dose of conjugated estrogens is 0.45 mg or 0.625 mg. In still yet another embodiment, the conjugated estrogens is administered once a day.

In still yet another aspect of the invention, the progestogen is progesterone, which is used cyclically (for the last 12 days of the 28-30 day cycle). In another embodiment, the dose of progesterone is 100 or 200 mg.

In still yet another aspect of the invention, the progestogen is norethindrone or norethindrone acetate. In another aspect, the dose of norethindrone or norethindrone acetate is 0.1 mg. In another aspect, the dose of norethindrone or norethindrone acetate is 0.5 mg. In another embodiment, the dose of norethindrone or norethindrone acetate is 1.0 mg. In yet another aspect, the norethindrone or norethindrone acetate is administered once a day.

In still yet another aspect of the invention, the progestogen is norgestimate. In another aspect, the dose of norgestimate is 0.09 mg. In still yet another aspect, the norgestimate is administered once a day.

In still yet another aspect of the invention, the progestogen is medroxyprogesterone. In still yet another aspect of the invention, the dose of medroxyprogesterone is 1.5 mg. In another aspect, the dose of medroxyprogesterone is 2.5 mg or 5 mg. In yet another aspect, the medroxyprogesterone is administered once a day.

In still yet another aspect of the invention, the progestogen is drospirenone. In another aspect, the dose of drospirenone is 0.25 mg. In still yet another aspect, the dose of drospirenone is 0.5 mg. In yet another aspect, the drospirenone is administered once a day.

In one aspect of the invention, the dose of Elagolix is 300 mg administered twice a day in combination with 0.5 mg estradiol and 0.1 mg norethindrone acetate.

In yet another aspect of the invention, the dose of Elagolix is 300 mg administered once or twice a day in combination with 1.0 mg estradiol and 0.5 mg norethindrone acetate.

In still yet another aspect of the invention, the dose of Elagolix is 400 mg administered once or twice a day in combination with 0.5 mg estradiol and 0.1 mg norethindrone acetate.

In still yet another aspect of the invention, the dose of Elagolix is 400 mg administered once or twice a day in combination with 1.0 mg estradiol and 0.5 mg norethindrone acetate.

In still yet another aspect of the invention, the dose of Elagolix is 600 mg administered once or twice a day in combination with 0.5 mg estradiol and 0.1 mg norethindrone acetate.

In still yet another aspect of the invention, the dose of Elagolix is 600 mg administered once or twice a day in combination with 1.0 mg estradiol and 0.5 mg norethindrone acetate.

The administration of Elagolix or a pharmaceutically acceptable salt or solvate thereof, and compositions and formulations thereof, may be prior to, immediately prior to, during, immediately subsequent to or subsequent to the administration of the estrogens and progestogens.

In still yet another aspect, the treatment cycle consist of daily administration of Elagolix and cyclical administration of progestogens in combination with a continuously administered estrogen. For example, the treatment cycle is 3 months or 6 months of daily administration of Elagolix and estrogens and progestogens are administered for the last 12-14 days of each month in order to mimic the normal menstrual cycle and induce regular, light bleeding episodes. In still yet another aspect, the treatment cycle consist of daily administration of Elagolix and estrogens and cyclical administration of progestogens.

In still yet a further aspect, the treatment cycle consist of daily administration of Elagolix and delayed administration of estrogens and/or progestogens. For example, the treatment cycle is 6 months of daily administration of Elagolix while estrogens and progestogens are administered daily for months 3-6. Alternatively, the treatment cycle is 12 months of daily administration of Elagolix while estrogens and progestogens are administered daily for months 3-12.

Methods of Practicing the Present Invention

In one embodiment of the invention, the dose of Elagolix, or a pharmaceutically acceptable salt thereof, is in the range of 100 to 800 mg, the range of 200 to 600 mg, the range of 200 to 400 mg, or the range of 300 to 600 mg. In a further embodiment of the invention, the dose of a compound of Elagolix or a pharmaceutically acceptable salt or solvate thereof, is about 75 mg, 100 mg, 150 mg, 200 mg, 300 mg, 400 mg, or 600 mg. The dose can be administered once a day or twice a day.

In one aspect of the invention, the methods are practiced by administering pharmaceutical compositions containing Elagolix or 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid. For the purposes of administration, 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid may be formulated as pharmaceutical compositions. Pharmaceutical compositions comprise 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid, or a pharmaceutically acceptable salt thereof, or a solvate thereof, and a pharmaceutically acceptable carrier and/or diluent. 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid is present in the composition in an amount which is effective to treat a particular disorder—that is, in an amount sufficient to achieve GnRH receptor antagonist activity, and preferably with acceptable toxicity to the patient.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

EXAMPLES

Summary of Efficacy and Safety Findings in Completed Phase 2 Studies in Endometriosis Subjects Efficacy Six Phase 2 randomized, double-blind, placebo-, and/or active-controlled, parallel-group, multiple dose studies were completed to evaluate elagolix as a treatment for endometriosis associated pain. Efficacy was assessed for dysmenorrhea (DYS), nonmenstrual pelvic pain (NMPP), dyspareunia, and general pelvic pain with a range of instruments.

Additional efficacy assessments included quality of life and the use of analgesics for control of endometriosis pain.

Across these Phase 2 studies, the enrollment criteria were similar and were intended to select premenopausal women aged 18 to 49 years of age with endometriosis confirmed by visual inspection (laparoscopy or laparotomy within 5 to 8 years of screening) who experienced moderate to severe endometriosis-associated pain. Women were included if they had regular menstrual cycles and no significant uterine fibroids or pelvic lesions.

Total daily doses of elagolix ranging from 75 to 250 mg were evaluated across a range of pain instruments measuring DYS, NMPP, or general pelvic pain (including patient global impression of change), during 12 or 24 weeks of treatment.

Collectively, these Phase 2 studies showed that elagolix daily doses of 100 to 250 mg were associated with clinically meaningful reductions in endometriosis-associated pain.

Studies also demonstrated that an elagolix daily dose of 150 mg had comparable effect to subcutaneous depot medroxyprogesterone acetate (DMPA-SC) on DYS and NMPP, while elagolix daily doses of 150 mg and 250 mg had less effect compared with leuprorelin.

Additionally, symptoms of dyspareunia were reduced and women reported improved quality of life assessments. Overall usage of analgesics for pain control also decreased in the elagolix treatment arms, The effects of elagolix on uterine bleeding were evaluated in the Phase 2 endometriosis program, with an analysis of the percentage of days of bleeding per month according to daily reporting of bleeding in an electronic diary (eDiary). These analyses showed. that overall, patients on elagolix experienced fewer days of bleeding per month compared with patients who received placebo; patients on 250 mg QD experienced fewer days of bleeding compared with patients on 150 mg QD. Review of individual menstrual charts from daily eDiary records showed that the majority of elagolix recipients experienced reduced bleeding intensity and often had extended intervals between bleeding episodes, Some subjects experienced periods of oligomenorrhea with some evidence of irregular bleeding as well, particularly at lower doses of elagolix.

Safety

The safety and tolerability of elagolix in women with endometriosis has been evaluated in 6 completed Phase 2 studies including 708 women who received at least 1 dose of elagolix. Overall, 475 women have received elagolix for at least 12 weeks and 278 women for a period of at least 24 weeks. The majority of women were Caucasian (78.9% to 100%), while approximately 7% were black and approximately 4.5% were Hispanic. The mean age across these six Phase 2 studies was 31 to 33 years (range 18 to 48 years) and mean body mass index (BMI) of 23 to 28 kg/m. Overall, 40% to 70% of women had received prior therapy for the treatment of endometriosis, and hormonal contraceptives were the most common class of drug prescribed for the condition. In addition, the majority were receiving analgesic medications (nonsteroidal anti-inflammatory drugs, opioids, and/or other) prior to study enrollment Review of the safety data in the completed Phase 2 studies in women with endometriosis indicates that elagolix was safe and well tolerated for all daily doses (100 to 250 mg) that were evaluated. The incidence of AEs (4.8%) that led to discontinuations was 4.8%, The most common adverse events observed with elagolix in both the 12-week and 24-week analysis sets were headache and nausea with an incidence similar to that observed with DMPA-SC in the 24-week analysis. None of these events were serious and they contributed to less than 1 % of study discontinuations.

Example 1

Effects on Bone Mineral Density (BMD)

Changes in BMD at the lumbar spine and the femur were evaluated over 24 weeks in three Phase 2 endometriosis studies. At the lumbar spine, mean BMD percent reductions from baseline appeared to be dose related: 0.11% to 1.29% at the 150 mg dose and 1.63% to 1.86% at the 250 mg dose. In the largest of these studies a small number of subjects, 2/55 (3.6%) in the 150 mg QD and 5/62 (8.1%) in the 75 mg BID regimens had decreases in BMD of the spine that exceeded 5% (no subject exceeded -8%) at 24 weeks. While a larger effect on BMD is anticipated with a 200 or 300 mg BID regimen compared to that observed with 250 mg QD dosed for 6 months in previous studies, the magnitude of this effect is unknown.

Example 2

Phase 2 Clinical Development Program for Uterine Fibroids

The global clinical development program is designed to support registration of elagolix (with add-back therapy) for the treatment of HMB associated with uterine fibroids in premenopausal women. The main objectives of the Phase 2 program for elagolix in premenopausal women with HMB associated with uterine fibroids are 1) to select the most appropriate dose(s) of elagolix to evaluate in Phase 2b and Phase 3, from both an efficacy and safety perspective, and 2) to assess the need for, adequacy and type of add-back therapy to be used in conjunction with elagolix. The first objective is the focus of the study described in this Example 2 and the second is the focus of a Phase 2b study.

While some women are likely to benefit (reduction in menstrual bleeding), even with low doses of elagolix, one of the key objectives of the study described in this Example 2 was to identify a dose of elagolix that provided robust efficacy (responder rates of greater than 80% for the composite bleeding assessment) and an acceptable safety and bleeding profile for the majority of women.

This example is a Phase 2a, multicenter, double-blind, placebo-controlled, randomized trial (N=280) with a 3-month treatment duration evaluating the safety and efficacy of Elagolix administered with or without Activella® in premenopausal women with uterine fibroids.

It evaluates the safety and efficacy of 6 doses of Elagolix (100 mg BID, 200 mg BID, 200 mg BID plus low dose Activella® (a combination of 0.5 mg estradiol and 0.1 mg northindrone acetate), 300 mg BID, 300 mg BID plus 1.0 mg of Estrace and 200 mg cyclical Prometrium (collectively referred to as "EP"), 400 mg QD and 600 QD) versus placebo (PBO) to reduce uterine bleeding associated with uterine fibroids and to reduce fibroid volume and uterine volume in premenopausal women 20 to 49 years of age with heavy menstrual bleeding (HMB; >80 mL blood loss per menstrual cycle). The study involved the following six (6) cohorts:

Cohort 1: Elagolix 200 mg BID or placebo (PBO).
Cohort 2: Elagolix 300 mg BID or placebo.
Cohort 3: Elagolix 200 mg BID plus low dose Activella® (a combination of 0.5 mg estradiol and 0.1 mg norethindrone acetate).
Cohort 4: Elagolix 100 mg BID, 400 mg QD or placebo.
Cohort 5: Elagolix 600 mg QD.
Cohort 6: Elagolix 300 mg BID plus estrogen (1.0 mg of estradiol (Estrace®)) and 200 mg progesterone (cyclical Prometrium®)) (EP). Estrace® was given daily with Elagolix (continuously) and Prometrium® was given daily for the last 12 days of each 28 day menstrual cycle (cyclical).

An exemplary administration schedule for Elagolix 300 mg BID alone or with add-back is shown in Table A. Subjects can self-administer drug twice a day (in the morning and in the evening approximately 12 hours apart). Drug should be taken orally twice daily for the treatment period (e.g., 6 months). For BID dosing with add-back, a morning dose of Elagolix and E/NETA (estradiol/norethindrone acetate) and an evening dose of Elagolix should be taken each day approximately 12 hours apart.

TABLE A

| Treatment Group | Treatments Administered | | | |
|---|---|---|---|---|
| | Investigational Product | | | |
| | Dosing Time | Elagolix 150 mg | Elagolix Placebo | E/NETA | Matching E/NETA Placebo |
| Elagolix Placebo | AM | 0 | 2 | 0 | 1 |
| | PM | 0 | 2 | 0 | 0 |
| Elagolix 300 mg BID | AM | 2 | 0 | 0 | 1 |
| | PM | 2 | 0 | 0 | 0 |
| Elagolix 300 mg BID plus E/NETA (low-dose)* | AM | 2 | 0 | 1 | 0 |
| | PM | 2 | 0 | 0 | 0 |
| Elagolix 300 mg BID plus E/NETA (standard-dose)** | AM | 2 | 0 | 1 | 0 |
| | PM | 2 | 0 | 0 | 0 |

*Estradiol/Norethindrone acetate 0.5 mg/0.1 mg (low-dose) capsules
**Estradiol/Norethindrone acetate 1.0 mg/0.5 mg (standard-dose) capsules Enrollment Preliminary data includes 170 women received at least 1 dose of Elagolix. Overall, 152 women have received Elagolix for at least 2 months and 127 women received Elagolix for 3 months (full treatment duration). The majority of women are black (~80%), with 19% Caucasian. The mean age is 41.9 years (range 28 to 53), and mean body mass index (BMI) is 30.3 kg/m$^2$.

The enrollment characteristics are shown in Table 1

TABLE 1

| Dose (Cohort) | Number of patients | | | | | | | | |
|---|---|---|---|---|---|---|---|---|---|
| | E300 BID (2) | E600 QD (5) | E300 BD + EP (6) | E200 BID (1) | E400 QD (4) | E200 BID + A (3) | E100 BID (4) | PBO* (1, 2, 4) | Total |
| Randomized | 30 | 30 | 27 | 35 | 32 | 34 | 33 | 50 | 271 |
| Treated | 30 | 30 | 27 | 35 | 32 | 34 | 33 | 50 | 271 |
| Completed | 26 | 24 | 25 | 28 | 26 | 29 | 26 | 43 | 227 |
| Discontinued | 4 | 6 | 2 | 7 | 6 | 5 | 7 | 7 | 44 |
| Interim Analysis Set | 30 | 30 | 27 | 35 | 32 | 34 | 33 | 50 | 271 |

Baseline characteristics are shown in Table 2.

TABLE 2

| Characteristic | Number of patients | | | | | | | | |
|---|---|---|---|---|---|---|---|---|---|
| | E 300 BID n = 30 | E 600 QD n = 30 | E 300 BID + EP N = 27 | E 200 BID n = 35 | E 400 QD n = 32 | E 200 BID + A n = 34 | E 100 BID n = 33 | PBO n = 50 | Total N = 271 |
| Mean Age (yrs.)* | 42.6 | 40.8 | 41.6 | 43.1 | 40.8 | 40.9 | 42.1 | 42.3 | 41.8 |
| Race White/Black (%) | 20/76.7 | 16.7/80 | 40.7/55.6 | 20.0/80.0 | 15.6/78.1 | 20.6/76.5 | 30.3/69.7 | 24.0/72.0* | 23.2/73.8 |
| Mean Weight (Kg) | 80.7 | 82.5 | 79.4 | 79.6 | 86.0 | 85.7 | 82.8 | 82.1 | 82.4 |
| Mean BMI (kg/m$^2$) | 29 | 31.1 | 29.6 | 29.4 | 31.7 | 31.8 | 30.4 | 29.9 | 30.3 |
| Menstrual Blood Loss (mL) - Mean (Median) | 208 (186) | 216 (179.7) | 265.8 | 333 (193) | 210 (192) | 245 (177) | 261 (210) | 336 (190) | 237 (163) |
| Hemoglobin (g/dL) - Mean | 11.2 | 10.8 | 10.3 | 10.8 | 11.0 | 10.8 | 10.2 | 10.4 | 10.7 |
| Primary Fibroid Volume (cm$^3$) Mean (Median) | 82.7 (47.8) | 86.7 (39.5) | 148.6 (99.3) | 137.9 (55.9) | 47 (27) | 66 (49) | 61 (27) | 101.1 (33.2) | 90.1 (41.1) |

TABLE 2-continued

| | Number of patients | | | | | | | | |
|---|---|---|---|---|---|---|---|---|---|
| Characteristic | E 300 BID n = 30 | E 600 QD n = 30 | E 300 BID + EP N = 27 | E 200 BID n = 35 | E 400 QD n = 32 | E 200 BID + A n = 34 | E 100 BID n = 33 | PBO n = 50 | Total N = 271 |
| Uterine Volume (cm$^3$) - Mean (Median) | 575 (519) | 495.7 (364.4) | 658.9 (616.8) | 685 (460) | 416 (322) | 529 (469) | 473 (297) | 493 (351) | 534 (421) |

Sex: All female
*age range 28-53; 15% are >25-≤35; 55% are >35-≤45; and 30% are >45
Note:
Asian ethnicity, missing data on race and multi-racial subjects account for remaining % on for race Efficacy There are a number of efficacy endpoints, but a composite endpoint consisting of two bleeding assessments was used to assess one measure of efficacy. It included the percent of subjects who achieved a menstrual blood loss (MBL) volume of <80 mL at the Final Month (last 28 days of treatment), and also achieved a ≥50% reduction in MBL volume from baseline to the Final Month (last 28 days of treatment) as measured by the Alkaline Hematin (AH) method. Eighty-five percent (85%), 97%, and 30% of subjects achieved the composite bleeding assessment endpoint in the 200 mg BID, 300 mg BID, and placebo groups, respectively (P<0.05 for 200 mg BID versus placebo in cohort 1, and 300 mg BID versus placebo in cohort 2). Eighty-two percent (82%) of subjects in the 200 mg BID+ low-dose Activella® (low dose Activella® is a combination of (a combination of 0.5 mg estradiol and 0.1 mg norethindrone acetate) group achieved this composite endpoint. With respect to fibroid and uterine volumes, 63%, 55%, and 29% of subjects achieved a ≥25% reduction in fibroid volume and 50%, 68%, and 9% achieved a ≥25% reduction in uterine volume in the 200 mg BID, 300 mg BID, and placebo groups, respectively. In the 200 mg BID+low dose group, 53% and 42% of subjects achieved a ≥25% reduction in fibroid and uterine volume, respectively. Quality of life (QoL) measures were also determined using the "Responsiveness of the uterine fibroid symptom and health-related quality of life questionnaire" (UFS-QOL) (Harding, Gale, Coyne Karin S., Thompson Christine L., Spies James B, United BioSource Corporation, 7101 Wisconsin Avenue, Suite 600, Bethesda, Md., 20814, USA, Health and Quality Life Outcomes, 2008, 6, page 99).

The results are summarized in FIGS. 1-5 as well as Tables 3 and 4 below. Table 3: Total Menstrual Blood Loss during the Treatment Period Measured by Alkaline Hematin (AH) Method (See, also FIG. 2).

TABLE 3

| Dose | Average Total Blood Loss Measured by AH Method During Treatment (in mL) |
|---|---|
| Elagolix 600 QD (N = 24) | 69.6 |
| Elagolix 300 BID (N = 26) | 4.3 |
| Elagolix 400 QD (N = 26) | 38.4 |
| Elagolix 200 BID (N = 28) | 47.0 |
| Elagolix 200 BID + Act (N = 29) | 119.8 |
| Elagolix 300 BID + EP (N = 25) | 114.5 |
| Elagolix 100 BID (N = 26) | 198.4 |
| Placebo (PBO) (N = 43) | 569.7 |

TABLE 4

Table 4: Average monthly Menstrual Blood Loss (MBL) during the Treatment Period Measured by Alkaline Hematin (AH) Method

| Dose | Number of subjects (N) | Average Blood Loss Per Cycle Measured by AH Method in Screening (mL) | Average total MBL from days 6-35 post-baseline (mL) | Average Total MBL from Days 36-65 Post-Baseline (mL) | Average Total MBL in Days 66-95 Post-Baseline (mL) |
|---|---|---|---|---|---|
| Elagolix 600 QD (N = 24) | 24 | 228.7 | 27.6 | 35.0 | 14.9 |
| Elagolix 300 BID (N = 26) | 26 | 224.8 | 0 | 0 | 4.3 |
| Elagolix 400 QD (N = 26) | 26 | 220.3 | 14.9 | 12.4 | 21.6 |
| Elagolix 200 BID (N = 28) | 28 | 287.4 | 0 | 5.5 | 41.5 |
| Elagolix 200 BID + Act (N = 29) | 29 | 251.9 | 26.3 | 41.5 | 37.9 |
| Elagolix 300 BID + EP (N = 25) | 25 | 253.9 | 32.7 | 40.2 | 46.2 |
| Elagolix 100 BID (N = 26) | 26 | 276.4 | 33.2 | 100.9 | 65.4 |
| Placebo (PBO) (N = 43) | 43 | 271.2 | 190.5 | 194.6 | 190.3 |

Figure 2:
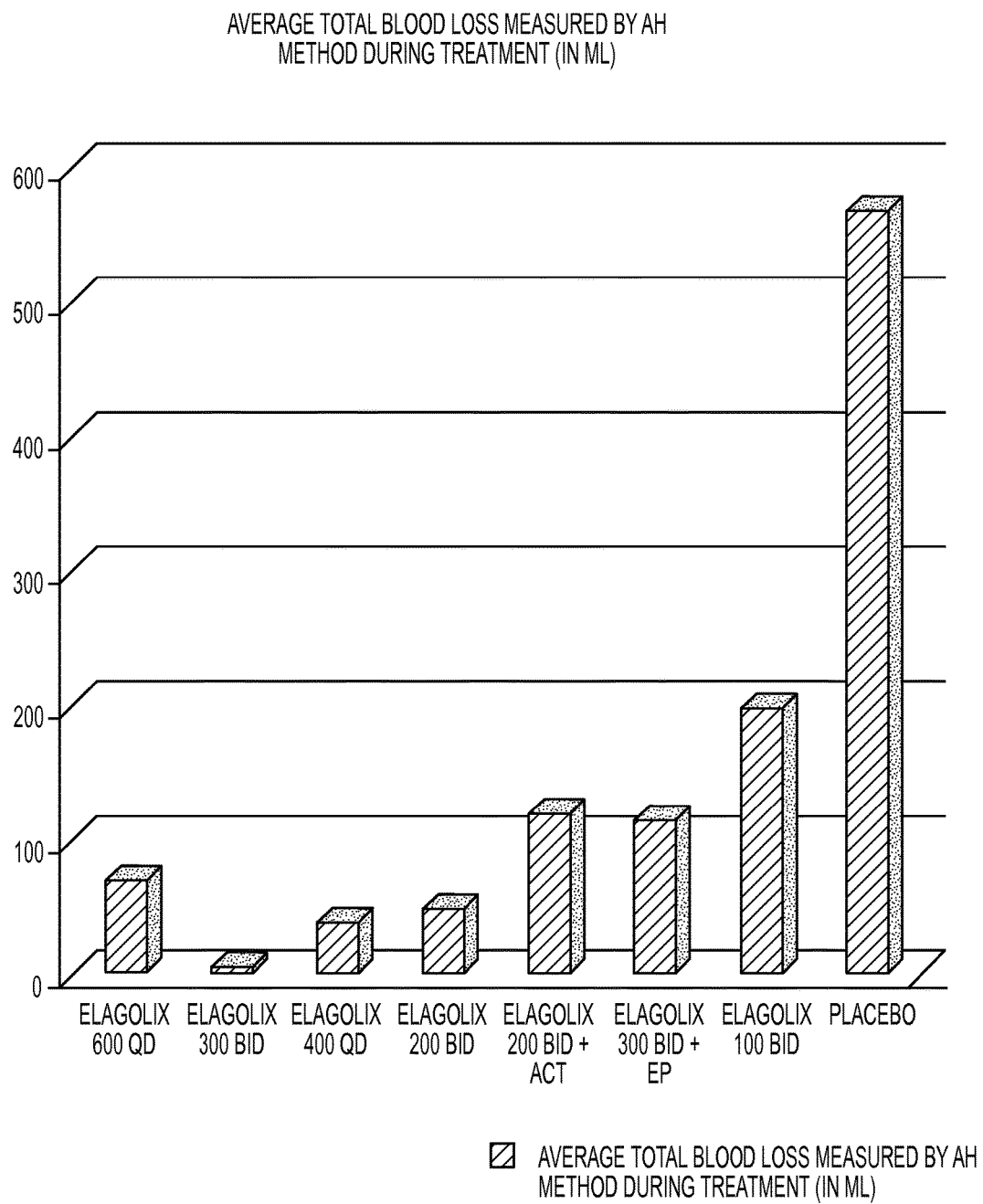
FIG. 2 shows the average total blood loss measured by the alkaline hematin methods during three (3) months of treatment as described in the study in Example 1. Patients were treated with Elagolix 600 QD (N=24), Elagolix 300 BID (N=26), Elagolix 400 QD (N=26), Elagolix 200 BID (N=28), Elagolix 200 BID plus low dose Activella® (a combination of 0.5 mg estradiol and 0.1 mg northindrone acetate), Elagolix 300 BID plus estrogen (1.0 mg of estradiol (Estrace®)) and 200 mg progesterone (cyclical Prometrium®) (collectively referred to as "EP") (N=25); Elagolix 100 BID (N=26) and placebo (PBO) (N=43).
Figure 3:
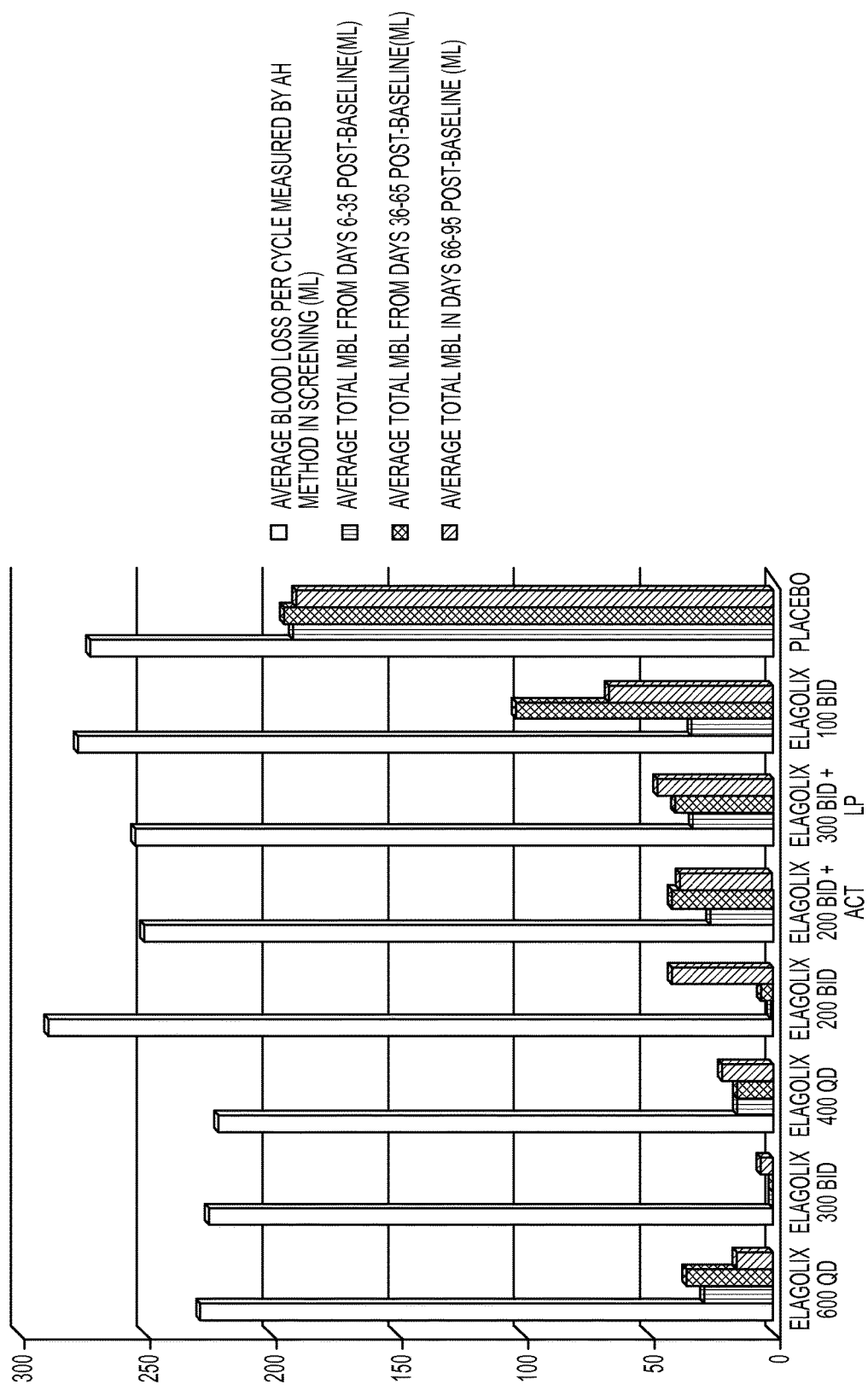
FIG. 3 shows an analysis of the average monthly blood loss (MBL) measured by the alkaline hematin methods during three (3) months of treatment as described in the study in Example 1. Patients were treated with Elagolix 600 QD, Elagolix 300 BID, Elagolix 400 QD, Elagolix 200 BID, Elagolix 200 BID plus low dose Activella® (a combination of 0.5 mg estradiol and 0.1 mg northindrone acetate), Elagolix 300 BID plus estrogen (1.0 mg of estradiol (Estrace®)) and 200 mg progesterone (cyclical Prometrium®); Elagolix 100 BID and placebo. For each of the eight (8) doses shown in FIG. 3, 4 bars are shown. The bar farthest to the left shows the average blood loss per cycle measured by AH method in screening (mL). The second bar is the average total MBL from days 6-35 post-baseline (mL). The third bar is the average total MBL from days 36-65 post-baseline (mL). The fourth bar (furthest to the right) is the average total MBL in days 66-95 post-baseline (mL).

The results in Tables 3 and 4 and FIGS. 1-3 show that Elagolix 300 mg BID without add-back therapy provides the maximum inhibition of bleeding (most of women achieved amenorrhea). Elagolix 400 mg QD and 600 mg QD were slightly less effective in this respect. However, these doses were associated with a relatively high percentage of hot flashes (50-62.5% of women reported an adverse event of hot flash). Elagolix 200 mg plus low-dose Activella® (0.5 mg E2/0.1 mg NETA) and elagolix 300 mg BID plus cyclical EP regimen (1 mg E2/200 mg progesterone for last 12 days of the cycle) restored HMB to normal levels. Both add-back regimens reduced the rate of hot flashes by approximately 50%.

Figure 4:
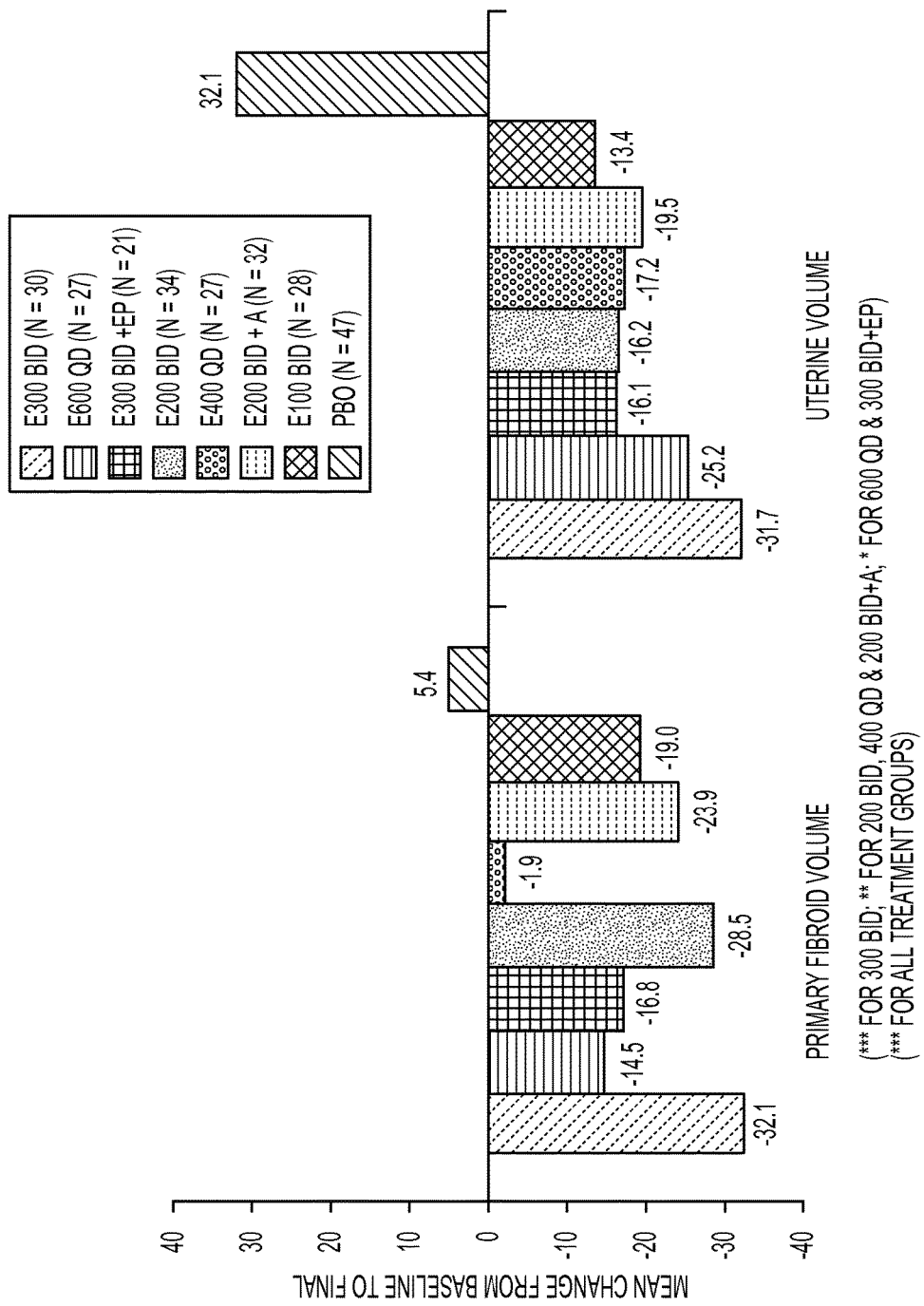
FIG. 4 shows an analysis of the mean percentage (%) change from baseline on each of primary fibroid and uterine volume as described in the study in Example 1. For the primary fibroid volume and uterine volume data shown in FIG. 4, patients were treated with Elagolix 300 BID (N=30) (first bar on the far left), E600 QD (N=27) (second bar from the left), E300+estrogen (1.0 mg of estradiol (Estrace®)) and 200 mg progesterone (cyclical Prometrium®) (referred to as "EP") (N=21) (third bar from the left), E200 BID (N=34) (fourth bar from the left), E400 QD (N=27) (fifth bar from the left), E200 BID+a low dose Activella® (a combination of 0.5 mg estradiol and 0.1 mg northindrone acetate) (referred to as "A") (N=32) (sixth bar from the left), E100 BID (seventh bar from the left) (N=28) and placebo (PBO) (N=47) (eighth bar from the left (or first on the right)). P values are defined as: *p<0.001 for Elagolix vs. pooled placebo (PBO; PBO from cohorts 1, 2 & 4). p<0.01 for Elagolix vs. pooled PBO (PBO from cohorts 1, 2 & 4). *p<0.05 for Elagolix vs. pooled placebo (PBO; PBO from cohorts 1, 2 & 4).
Figure 5:
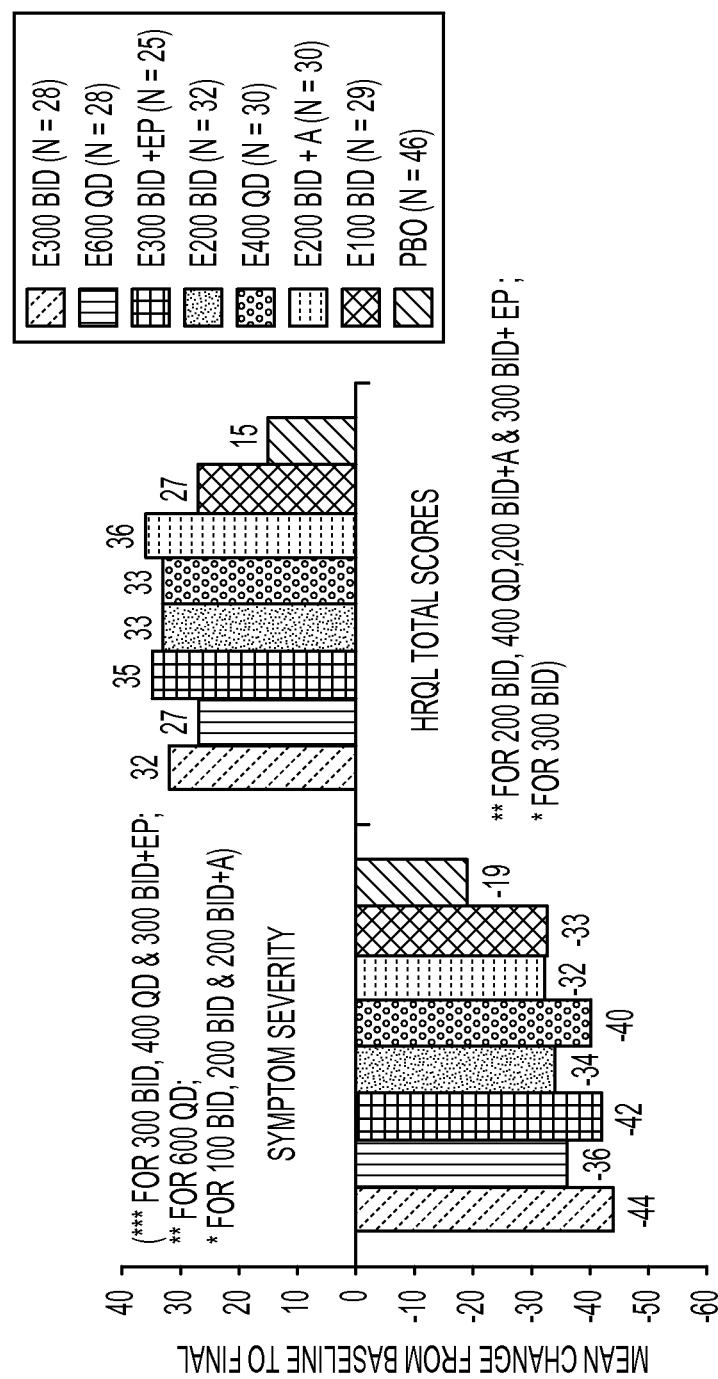
FIG. 5 shows an analysis of uterine fibroid symptom severity and quality of life (UFS-QoL) results as described in the study in Example 1. For the symptom severity and Health Related Quality of Life (HRQL) total scores and uterine volume data shown in FIG. 5, patients were treated with Elagolix 300 BID (N=28) (first bar on the far left), E600 QD (N=28) (second bar from the left), E300+estrogen (1.0 mg of estradiol (Estrace®)) and 200 mg progesterone (cyclical Prometrium®) (referred to as "EP") (N=25) (third bar from the left), E200 BID (N=32) (fourth bar from the left), E400 QD (N=30) (fifth bar from the left), E200 BID+a low dose Activella® (a combination of 0.5 mg estradiol and 0.1 mg northindrone acetate) (referred to as "A") (N=30) (sixth bar from the left), E100 BID (seventh bar from the left) (N=29) and placebo (PBO) (N=46) (eighth bar from the left (or first on the right)). P values are defined as: *p<0.001 for Elagolix vs. pooled placebo (PBO; PBO from cohorts 1, 2 & 4). p<0.01 for Elagolix vs. pooled PBO (PBO from cohorts 1, 2 & 4). *p<0.05 for Elagolix vs. pooled placebo (PBO; PBO from cohorts 1, 2 & 4).

FIG. 4 shows that all Elagolix treatments (with and without add-back therapy) reduced uterine and fibroid volumes within 3 months and Elagolix 300 mg BID showed the strongest effects. Additionally, both add-back therapy regimens did not substantially reduced Elagolix effects on volume reduction. FIG. 5 shows that All Elagolix treatments (with or without add-back therapy) showed an improvement in quality of life (QoL) measures compared to placebo.

On the basis of preliminary data from the interim analysis of the study described in this Example 2, the dose of elagolix selected for the Phase 2b study is 300 mg BID (>80% responder rate on composite bleeding assessment endpoint).

At the proposed elagolix study dose of 300 mg BID, add-back therapy is likely needed to minimize bone loss and vasomotor symptoms associated with low estradiol (E2) levels.

Low-dose generic Activella (E/NETA) is a continuous combined oral Estrogen/Progestin regimen containing low-dose estrogen (E2 0.5 mg) and progestin (NETA 0.1 mg) that is approved as a postmenopausal hormone replacement therapy.

Standard-dose generic Activella (E/NETA) is a continuous combined oral Estrogen/Progestin regimen containing low-dose estrogen (E2 1.0 mg) and progestin (NETA 0.5 mg) that is approved as a postmenopausal hormone replacement therapy.

Preliminary results from this Example 2 after 3 months of treatment provide further evidence that elagolix doses of 400 to 600 mg/day are likely to be effective and provide an acceptable safety profile in this study population, and that Activella (or its generic equivalent), as an add-back regimen, is an appropriate option for further evaluation in order to mitigate the side effects of estrogen deprivation.

What is claimed is:

1. A method for managing heavy menstrual bleeding in a subject suffering from heavy menstrual bleeding, the method comprising
orally administering to said subject for a period of at least 84 days
(a) 4-((R)-2-[5-(2-fluoro-3-methoxy-phenyl)-3-(2-fluoro-6-trifluoromethylbenzyl)-4-methyl-2, 6-dioxo-3,6-dihydro-2H-pyrimidin-1-yl]-1-phenyl-ethylamino)-butyric acid as a sodium salt, wherein the sodium salt is administered in an amount equivalent to 600 mg per day of the free acid, wherein the sodium salt is administered twice daily in a first dose equivalent to about 300 mg of the free acid and a second dose equivalent to about 300 mg of the free acid;
(b) 1.0 mg per day of estradiol; and
(c) 0.5 mg per day of norethindrone acetate;
wherein the method reduces the volume of menstrual blood loss in the subject to less than 80 mL per cycle and by at least 50% from baseline.

2. The method of claim 1, wherein the sodium salt is administered for at least 168 days.

3. The method of claim 2, wherein the sodium salt is administered for about 168 days to about 1 year.

4. The method of claim 1, wherein the subject has uterine fibroids.

5. The method of claim 1, wherein the subject does not have uterine fibroids.

6. The method of claim 5, wherein the subject has adenomyosis.

7. A method for managing heavy menstrual bleeding associated with uterine fibroids in a subject in need thereof, the method comprising:
orally administering to said subject for a period of at least 84 days
(a) 4-((R)-2-[5-(2-fluoro-3-methoxy-phenyl)-3-(2-fluoro-6-trifluoromethylbenzyl)-4-methyl-2, 6-dioxo-3,6-dihydro-2H-pyrimidin-1-yl]-1-phenyl-ethylamino)-butyric acid as a sodium salt, wherein the sodium salt is administered in an amount equivalent to 600 mg per day of the free acid,
wherein the sodium salt is administered twice daily in a first dose equivalent to about 300 mg of the free acid and a second dose equivalent to about 300 mg of the free acid;
(b) 1.0 mg per day of estradiol, once daily; and
(c) 0.5 mg per day of norethindrone acetate, once daily;
wherein the method reduces the volume of menstrual blood loss in the subject to less than 80 mL per cycle and by at least 50% from baseline.

8. The method of claim 7, wherein the sodium salt is administered for at least 84 days and up to about 168 days.

9. The method of claim 7, wherein the estradiol and norethindrone acetate are administered simultaneously with the first or second dose of the sodium salt.

10. A method for managing heavy menstrual bleeding associated with uterine fibroids in a subject in need thereof, the method comprising:
orally administering to the subject for a period of at least 84 days and not to exceed 24 months
(1) a first dosage form comprising
(a) 4-((R)-2-[5-(2-fluoro-3-methoxy-phenyl)-3-(2-fluoro-6-trifluoromethylbenzyl)-4-methyl-2, 6-dioxo-3,6-dihydro-2H-pyrimidin-1-yl]-1-phenyl-ethylamino)-butyric acid as a sodium salt, wherein the sodium salt is present in the first dosage form in an amount equivalent to 300 mg of the free acid;
(b) 1.0 mg of estradiol; and
(c) 0.5 mg of norethindrone acetate; and
(2) a second dosage form comprising
(a) 4-((R)-2-[5-(2-fluoro-3-methoxy-phenyl)-3-(2-fluoro-6-trifluoromethylbenzyl)-4-methyl-2, 6-dioxo-3,6-dihydro-2H-pyrimidin-1-yl]-1-phenyl-ethylamino)-butyric acid as a sodium salt, wherein the sodium salt is present in the second dosage form in an amount equivalent to 300 mg of the free acid;
wherein the first and second dosage forms are each administered once daily and the first and second dosage forms are administered in approximately the morning and evening of each day, respectively;
wherein the method reduces the volume of menstrual blood loss in the subject to less than 80 mL per cycle and by at least 50% from baseline.

11. The method of claim 10, wherein the sodium salt is administered for at least 84 days and up to about 168 days.

12. A method for managing heavy menstrual bleeding associated with uterine fibroids in a subject in need thereof, the method comprising:

orally administering to said subject for a period of at least 84 days a three drug regimen comprising:
- (a) 4-((R)-2-[5-(2-fluoro-3-methoxy-phenyl)-3-(2-fluoro-6-trifluoromethylbenzyl)-4-methyl-2, 6-dioxo-3,6-dihydro-2H-pyrimidin-1-yl]-1-phenyl-ethylamino)-butyric acid as a sodium salt, wherein the sodium salt is administered in an amount equivalent to 600 mg per day of the free acid, wherein the sodium salt is administered twice daily in a first dose equivalent to about 300 mg of the free acid and a second dose equivalent to about 300 mg of the free acid;
- (b) 1.0 mg per day of estradiol, once daily; and
- (c) 0.5 mg per day of norethindrone acetate, once daily;

wherein the method reduces the volume of menstrual blood loss in the subject to less than 80 mL per cycle and by at least 50% from baseline; and wherein the method limits bone mineral density loss from baseline in the subject to less than 8%.

13. The method of claim 12, wherein the sodium salt is administered for at least 84 days and up to about 168 days.

14. The method of claim 12, wherein the estradiol and norethindrone acetate are administered simultaneously with the first or second dose of the sodium salt.

15. The method of claim 12, wherein the method limits bone mineral density loss from baseline in the subject to less than 5%.

16. The method of claim 12, comprising continuing to orally administer the three drug regimen for a time period as needed to manage the heavy menstrual bleeding associated with uterine fibroids, the time period not to exceed 24 months.

* * * * *